(12) United States Patent
O'Malley et al.

(10) Patent No.: US 6,486,310 B1
(45) Date of Patent: Nov. 26, 2002

(54) GENE ENCODING THE RAT DOPAMINE $D_4$ RECEPTOR

(75) Inventors: Karen L. O'Malley; Richard D. Todd, both of St. Louis, MO (US)

(73) Assignee: Washington University, St. Louis, MO (US)

( * ) Notice: Subject to any disclaimer, the term of this patent is extended or adjusted under 35 U.S.C. 154(b) by 0 days.

(21) Appl. No.: 08/261,293

(22) Filed: Jun. 16, 1994

Related U.S. Application Data

(63) Continuation of application No. 08/014,013, filed on Jan. 28, 1993, now abandoned.

(51) Int. Cl.⁷ .............................................. C12N 15/12
(52) U.S. Cl. .................. 536/23.5; 435/69.1; 435/252.3; 435/320.1; 536/24.31
(58) Field of Search ............................ 435/69.1, 252.3, 435/320.1; 566/23.5; 536/24.31

(56) References Cited

PUBLICATIONS

Benes, F.M., et al., "Quantitative Cytoarchitectural Studies of the Cerebral Cortex of Schizophrenics", 43 *Arch. Gen. Psychiatry* 31–35 (1986).
Brodde, O., "Physiology and Pharmacology of Cardiovascular Catecholamine Receptors: Implications for Treatment of Chronic Heart Failure". 120 *American Heart Journal* 1565–1572 (1990).
Bunzow, J.R., et al., "Cloning and Expression of a Rat $D_2$ Dopamine Receptor cDNA", 336 Nature 783–787 (1988).
Chan, Y., et al., "The Nucleotide Sequence of a Rat 18 S Ribosomal Ribonucleic Acid Gene and a Proposal for the Secondary Structure of 18 S Ribosomal Ribonucleic Acid", 259 *The Journal of Biological Chemistry* 224–230 (1984).
Chen, C. and H. Okayama, "High–efficiency Transformation of Mammalian Cells by Plasmid DNA", 7 *Molecular and Cellular Biology* 2745–2752 ((1987).
Chen E.Y. and P. H. Seeburg, "Supercoil Sequencing: A Fast and Simple Method for Sequencing Plasmid DNA", 4 *DNA* 165–170 (1985).
Choi, H.K., et al., "Immortalization of Embryonic Mesencephalic Dopaminergic Neurons by Somatic Cell Fusion", 552 *Brain Research* 67–76 (1991).
Chomczynski, P. and N. Sacchi, "Single–step Method of RNA Isolation by Acid Guanidinium Thiocyanate–Phenol–Chloroform Extraction", 162 *Analytical Biochemistry* 156–159 (1987).
Cohen, A.I., et al., "Photoreceptors of Mouse Retinas Possess $D_4$ Receptors Coupled to Adenylate Cyclase", 89 *Proc. Natl. Acad. Sci. USA* 12093–12097 (1992).
Dearry, A., et al., "Molecular Cloning and Expression of the Gene for a Human $D_4$ Dopamine Receptor", 347 *Nature* 72–76 (1990).

Feinberg, A.P. and B. Vogelstein, "A Technique for Radiolabeling DNA Restriction Endonuclease Fragments to High Specific Activity", 137 *Analytical Biochemistry* 266–267 Addendum (1984).
Fitton, A. and R.C. Heel, "Clozapine A Review of its Pharmacological Properties, and Therapeutic Use in Schizophrenia", 40 (5) *Drugs* 722–747 (1990).
Gandelman, K., et al., "Species and Regional Differences in the Expression of Cell–Type Specific Elements at the Human and Rat Tyrosine Hydroxylase Gene Loci", 55 *J. Neurochem.* 2149–2152 (1990).
Gelernter, J., "The D4 Dopamine Receptor (DRD4) Maps to Distal 11p Close to HRAS", 13 *Genomics* 208–210 (1992).
Giros, B., et al., "Shorter Variants of the $D_3$ Dopamine Receptor Produced Through Various Patterns of Alternative Splicing", 176 *Biochemical and Biophysical Research Communications* 1584–1592 (1991).
Goldberg, L.I. and J.D. Kohli, "Identification and Characterization of Dopamine Receptors in the Cardiovascular System", 32(12) *Cardiologia* 1603–1607 (1987).
Graham, F. L. and A.J. Van Der Eb, "A New Technique for the Assay of Infectivity of Human Adenovirus 5 DNA", 52 *Virology* 456–467 (1973).
Hamblin, M.W., et al., "Interactions of Agonists with D–2 Dopamine Receptors: Evidence for a Single Receptor Population Existing in Multiple Agonist Affinity–States in Rat Striatal Membranes", 33 *Biochemical Pharmacology* 877–887 (1984).
Y. Jeste and J.B. Lohr, "Hippocampal Pathologic Findings on Schizophrenia", 46 *Gen. Psychiatry* 1019–1024 ((1989).
Keating, M., et al., "Linkage of a Cardiac Arrhythmia, the Long QT Syndrome, and the Harvey ras–1 Gene", 252 *Science* 704–706 ((1991).

(List continued on next page.)

Primary Examiner—John Ulm
(74) Attorney, Agent, or Firm—Holland & Knight LLP

(57) ABSTRACT

A gene, flanking 5' and 3' sequences and derived cDNA encoding a rat $D_4$ dopamine receptor that is predominantly located in the cardiovascular and retinal systems is disclosed. The cDNA has been expressed in transfected mammalian cells and demonstrated to preferentially bind dopamine antagonists such as clozapine. The cDNA is useful as a probe for related $D_4$ dopamine receptors. Expressed in appropriate cell lines, it is useful as an in vitro screen for drugs which specifically bind to the receptor. Drugs that specifically bind to the receptor are then screened using standard methodology in rats, mice or dogs, for the physiological effects. Amino acids deduced from the determination of cDNA can be used to generate either polyclonal or monoclonal antibodies which recognize the $D_4$ receptor sequence but do not recognize $D_1$, $D_2$, $D_3$ or $D_5$ dopamenergic receptors, for use in immunocytochemical studies, and for identification and isolation via flow sorting of D4 expressing cell types. Antibodies could also be used to block or modify the effects of D4 agonists and/or antagonists. It is also demonstrated that selective stimulation or inhibition of some dopamine receptors, including $D_4$, can be used to induce changes in the morphology of cells such as neurons.

4 Claims, 8 Drawing Sheets

OTHER PUBLICATIONS

Kebabian, J.W. and D.B. Caine, "Multiple Receptors for Dopamine", 277 *Nature* 93–96 (1979).

Kohli, J.D., et al., "Dopamine Receptors in the Stellate Ganglion of the Dog", 164 *European Journal of Pharmacology* 265–272 (1989).

Krug, M.S. and S.L. Berger, "First–Strand cDNA Synthesis Primed with Oligo(dT)", 152 *Methods in Enzymology* 316–325 (1987).

Mack, K.J., "The Mouse Dopamine $D2_A$ Receptor Gene: Sequence Homology With the Rat and Human Genes and Expression of Alternative Transcripts", 57 *J. Neurochem.* 795–801 (1991).

McCoy, C.E., et al., "Selective Antagonism of the Hypotensive Effects of Dopamine Agonists in Spontaneously Hypertensive Rats", 8 *Hypertension* 298–302 ((1986).

Monsma, Jr., F.J., et al., "Molecular Cloning and Expression of a $D_1$ Dopamine Receptor Linked to Adenylyl Cyclase Activation", 87 *Proc. Natl. Acad. Sci. USA* 6723–6727 (1990).

Niznik, H.B., "Dopamine Receptors: Molecular Structure and Function", 54 *Molecular and Cellular Endocrinology* 1–22 (1987).

O'Malley, K.L., et al., "The Rat Dopamine $D_4$ Receptor: Sequence, Gene Structure, and Demonstration of Expression in the Cardiovascular System", 4 *The New Biologist* 137–146 (1992).

O'Malley, K.L., et al., "Organization and Expression of the Rat $D2_A$ Receptor Gene: Identification of Alternative Transcripts and a Variant Donor Splice Site", 29 *Biochemistry* 1367–1371 (1990).

Pfefferbaum, A., et al., "Computed Tomographic Evidence for Generalized Sulcal and Ventricular Enlargement is Schizophrenia", 45 *Arch. Gen. Psychiatry*, 633–640 (1988).

Seeman, P., et al., "Conversion of Dopamine $D_1$ Receptors From High to Low Affinity for Dopamine", 34 Biochem. Pharmac. 151–154 (1985).

Sikich, L., et al., "$5-HT_{1A}$ Receptors Control Neurite Branching During Development", 56 Developmental Brain Research 269–274 (1990).

Sokoloff, P., et al., "Molecular Cloning and characterization of a Novel Dopamine Receptor ($D_3$) As a Target for Neuroleptics", 347 *Nature* 146–151 (1990).

Springer, J.E., et al., "Non–radioactive Detection of Nerve Growth Factor Receptor (NGFR) mRNA in Rat Brain Using In Situ Hybridization Histochemistry", 39 *The Journal of Histochemistry and Cytochemistry* 231–234 (1991).

Sunahara, R.K., et al., "Cloning of the Gene For a Human Dopamine $D_5$ Receptor With Higher Affinity For Dopamine Than $D_1$ ", 350 *Nature* 614–619 (1991).

Sunahara, R.K., et al., "Human Dopamine $D_1$ Receptor Encoded By An Intronless Gene on Chromosome 5", 347 *Nature* 80–83 (1990).

Todd, R.D., "Neural Development is Regulated by Classical Neurotransmitters: Dopamine D2 Receptor Stimulation Enhances Neurite Outrowth", 31 *Biol. Psychiatry* 794–807 (1992).

Todd, R.D., et al., "Cloning of Ligand–Specific Cell Lines Via Gene Transfer: Identification of a $D_2$ Dopamine Receptor Subtype", 86 *Proc. Natl. Acad. Sci. USA* 10134–10138 (1989).

Van Tol, H.H.M., et al., "Multiple Dopamine D4 Receptor Variants in The Human Population", 358 *Nature* 149–152 (1992).

Van Tol, H.H.M., et al., "Cloning of the Gene for a Human Dopamine $D_4$ Receptor With High Affinity for the Antipsychotic Clozapine", 350 *Nature* 610–614 (1991).

Wigler, M., et al., "Transformation of Mammalian Cells with Genes From Procaryotes and Eucaryotes", 16 *Cell* 777–785 (1979).

Zhao, R., et al., "Effects of Dopamine $D_1$ and Dopamine $D_2$ Receptor Agonists on Coronary and Peripheral Hemodynamics", 190 *European Journal of Pharmacology* 193–202 (1990).

Zhou, Q., et al., "Cloning and Expression of Human and Rat $D_1$ Dopamine Receptors", 347 *Nature* 76–80 (1990).

Nature 350:610–614, Apr. 18, 1991, Van Tol et al Cloning of the gene for a human dopamine D4 receptor with high affinity for the antipsychiatric clozapine.*

Nature 347:76–80, Sep. 6, 1990, 2 hou et. al cloning and expression of human and rat D1 dopamine receptors.*

* cited by examiner 200 bp rD4: MGNSSATGDGGLLAGRGPESLGTGT---GLGGAGAAALVGGVLLIGMVLAGNSLVCVS
hD4: MGNRSTADADGLLAGRGPAAGASAGASAGLAGQGAAALVGGVLLIGAVLAGNSLVCVS

TRANSMEMBRANE DOMAIN I rD4: VASERILQTPTNYFIVSLAAADLLLAVLVLPLFVYSE--GGVWLLSPRLCDTLMAMDV
hD4: VATERALQTPTNSFIVSLAAADLLLALLVLPLFVYSEVQGGAWLLSPRLCDALMAMDV

TRANSMEMBRANE DOMAIN II rD4: MLCTASIFNLCAISVDRFVAVTVPLRYNQQGQC--QLLIAATWLLSAAVAAPVVCGL
hD4: MLCTASIFNLCAISVDRFVAVAVPLRYNRQGGSRRQLLLIGATWLLSAAVAAPVLCGL

TRANSMEMBRANE DOMAIN III         TRANSMEMBRANE DOMAIN IV

FIG. 2A

```
                           TRANSMEMBRANE DOMAIN V
                           |---------------------|
rD4:  NDVPGRDPTVCCLEDRDYVVVYSSICSFFLPCPLMLLYWATFRGLRRWEAARHTKLHS
      ||| ||||| | ||||||||||| ||||||||||||||||||||| ||  |  |||
hD4:  NDVRGRDPAVCRLEDRDYVVVYSSVCSFFLPCPLMLLYWATFRGLQRWEVARRAKLHG rD4:  RAPRRPSGPGPPVSDPTQGPLFS------DCPPPSPSLRTSPTVSSRPESDLSQSPCSP
      |||||||||||||  ||| |||       |||     |     ||
hD4:  RAPRRPSGPGPPSPTPPAPRLPQDPCGPDCAPPAPGLPPD---------PCGS
                                                    *
                                         TRANSMEMBRANE DOMAIN VI
                                         |----------------------|
rD4:  GCLLPDA----ALAQPPAPSSRKKRGAKITGRERKAMRVLPVVVGAFLMCWTPFFVVH
       |  ||     | || ||| || |||||||||||||||||||||||| |||||||||
hD4:  NCAPPDAVRAAALPPQTPPQTRRRRAKITGRERKAMRVLPVVVGAFLLCWTPFFVVH

FIG. 2B
```

TRANSMEMBRANE DOMAIN VII rD4: ITRALCPACFVSPRLVSAVTWLGYVNSALNPIIYTIFNAEFRSVFRKTLRLRC hD4: ITQALCPACSVPPRLVSAVTWLGYVNSALNPVIYTVFNAEFRNVFRKALRACC

Amino acid alignment of rat (rD4) and human (hD4) $D_4$ receptors.

An asterisk marks the position of the additional splice site in the human gene.

FIG. 2C

GENE ENCODING THE RAT DOPAMINE $D_4$ RECEPTOR

This is a continuation of application Ser. No. 08/014,013, filed on Jan. 28, 1993, now abandonded.

The United States government has rights in this invention by virtue of a grant from the NIMH, grant number MH45019, to Richard D. Todd, principal investigator.

BACKGROUND OF THE INVENTION

The present invention is generally in the area of dopamine receptors, and is specifically a gene encoding a dopamine $D_4$ receptor, its flanking 5' and 3' sequences, and its derived cDNA, and methods of use thereof in screening for compounds having selective effects on the cardiovasculature and retinal tissues through interactions with the dopamine $D_4$ receptor.

Dopamine is an important neurotransmitter in the central nervous system (CNS), where it is thought to be involved in a variety of functions including motor coordination, reproductive regulation, and generation of emotions. A distinct peripheral dopaminergic system is thought to exist, although it is less well characterized. CNS dopamine receptors have historically been divided into two major classes, $D_1$ and $D_2$, which can be distinguished by pharmacological, functional, and physical characteristics (Kebabian and Calne, (1979) "Multiple receptors for dopamine" *Nature* 277:93–96; Hamblin et al., (1984) "Interactions of agonists with $D_2$ dopamine receptors: evidence for a single receptor population existing in multiple agonist affinity-states in rat striatal membranes" *Biochem. Pharmacol.* 33:877–887; Seeman et al., (1985) "Conversion of dopamine receptors from high to low affinity for dopamine" *Biochem. Pharmacol.* 34:151–154; Niznik, (1987) "Dopamine receptors: molecular structure and function" *Mol. Cell. Endocrinol.* 54:1–22). Peripheral dopamine receptors have been divided into DA1 and DA2 subgroups, which share some but not all pharmacological characteristics with their CNS counterparts (Goldberg and Kohli, (1987) "Identification and characterization of dopamine receptors in the cardiovascular system" *Cardiologia* 32:1603–1607; Kohli et al., (1989) "Dopamine receptors in the stellate ganglion of the dog" *Eur. J. Pharmacol.* 164:265–272; Brodde, (1990) "Physiology and pharmacology of cardiovascular catecholamine receptors; implications for treatment of chronic heart failure" *Am. Heart J.* 120:1565–1572).

Molecular cloning techniques have revealed a diversity of CNS receptor subtypes in each class. All are members of the G protein-coupled receptor gene superfamily and have seven potential transmembrane (Tm) spanning domains. In contrast to most members of the G-protein coupled receptor gene family, the $D_2$-like genes have multiple exons separated by introns both in the coding and non-coding regions. Further diversity is generated by alternative splicing.

Prototypic $D_2$ ligand binding and signal transduction characteristics have been found for $D_2$ (Bunzow et al., (1988) "Cloning and expression of a rat $D_2$ dopamine receptor cDNA" *Nature* 336:783–787) and $D_3$ (Sokoloff et al., (1990) "Molecular cloning and characterization of a novel dopamine receptor ($D_3$) as a target for neuroleptics" *Nature* 347:146–151) receptors. The recently reported human $D_4$ receptor also has a $D_2$-like pharmacological profile (Van Tol et al., (1991) "Cloning of the gene for a human dopamine $D_4$-receptor with high-affinity for the antipsychotic clozapine" *Nature* 350–610–614). Two distinct $D_1$ receptors have also been cloned, called $D_1$ (Sunahara et al., (1990) "Human dopamine $D_1$ receptor encoded by an intronless gene on chromosome 5" *Nature* 347:80–83; Zhou et al., (1990) "Cloning and expression of human and rat $D_1$ dopamine receptors" *Nature* 347:76–80; Monsma et al., (1990) "Molecular cloning and expression of a $D_1$ dopamine receptor linked to adenylyl cyclase activation" *Proc. Natl. Acad. Sci. USA* 87:6723–6727; Dearry et al., (1990) "Molecular cloning and expression of the gene for a human $D_1$ dopamine receptor" *Nature* 347:72–76) and $D_5$ (Sunahara et al., (1991) "Cloning of the gene for a human dopamine $D_5$ receptor with higher affinity for dopamine than $D^1$" *Nature* 350:614–619). To date no peripheral dopamine receptor has been cloned, although it has been suggested that there is a low level of expression of $D_3$ in kidney (Sokoloff et al., 1990).

Van Tol et al. (1991) reported the isolation of a human $D_4$ receptor with a high affinity for the neuroleptic drug clozapine. Multiple variants of this dopamine receptor were also reported by Van Tol, et al., (1992) *Nature* 358, 149–154. These receptors were also the subject of PCT WO 92/10571 by State of Oregon. Although the function of these particular receptors was not identified, they are assumed to be important in binding drugs having anti-psychotic activity.

It is an object of the present invention to provide the gene, its flanking 5' and 3' sequences and the derived cDNA encoding another dopamine $D_4$ receptor present in rat cells.

It is a further object of the present invention to provide methods for expression and screening of compounds binding the new dopamine $D_4$ receptor.

It is another object of the present invention to provide a method for screening for compounds having cardiovascular activity and effects on retinal tissue which specifically bind to dopamine $D_4$ receptors.

It is still another object of the present invention to provide a means and method for modulation of the morphology of cells expressing $D_4$ receptors, and other dopamine receptors, by stimulation or inhibition of the receptors via exposure of the cells to specific compounds.

SUMMARY OF THE INVENTION

A gene, its 5' and 3' flanking sequences and the derived cDNA encoding a rat $D_4$ dopamine receptor that is predominantly located in the cardiovascular and retinal systems is disclosed. The gene has been expressed in transfected mammalian cells and demonstrated to preferentially bind dopamine antagonists such as clozapine.

The gene and/or cDNA is useful as a probe for related $D_4$ dopamine receptors. Expressed in appropriate cell lines, it is useful as an in vitro screen for drugs which specifically bind to the receptor. Drugs that specifically bind to the receptor are then screened using standard methodology in rats, mice or dogs, for the physiological effects. Antibodies to the protein are useful in immunocyto chemical studies, identification and isolation via flow sorting of D4 expressing cell types, and in blocking or modifying the effects of D4 agonists and/or antagonists.

Stimulation or inhibition of the $D_4$ receptor, $D_2$ receptor, or $D_3$ receptor, either in cells naturally expressing the receptor or which have been transfected with cDNAs or genes encoding anyone or more of several dopamine receptors, has been demonstrated to allow modification of the cell morphology. In one example, the number and extent of branching of neurites in cells transfected with dopamine receptors is increased significantly by exposure to compounds selectively binding to the receptors.

BRIEF DESCRIPTION OF THE DRAWINGS

FIG. 2 shows the amino acid alignment of rat (rD4) and human (hD4) $D_4$ receptors.

FIG. 4 is a pharmacological analysis of transfected rat $D_{2444}$ and $D_4$ receptors and human $D_3$ receptors in CCL1.3 cells.

DETAILED DESCRIPTION OF THE INVENTION

Figure 1:
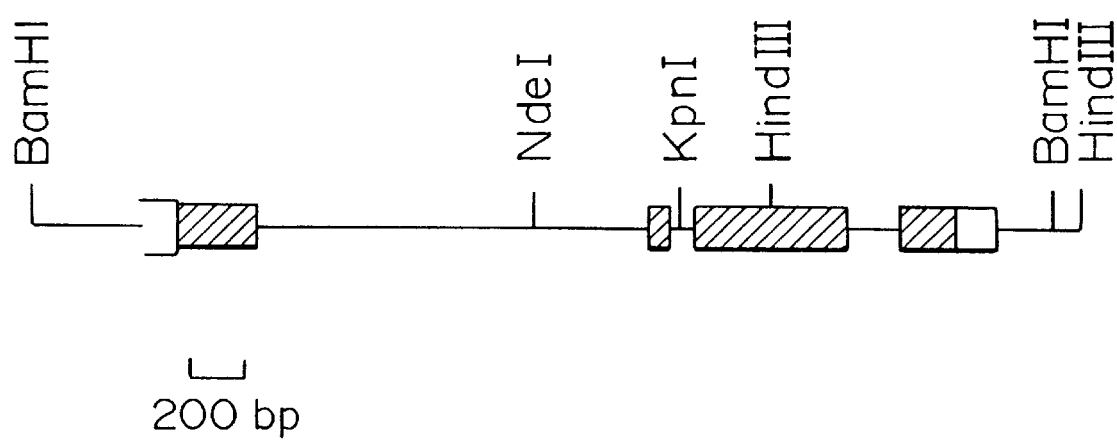
FIG. 1 is a schematic of the sequence structure of the rat dopamine $D_4$ receptor gene. Coding regions are shown in black, noncoding regions are shown as clear boxes, and relevant restriction sites are indicated.

Dopamine receptors have been implicated in a variety of neurological and neuropsychiatric disorders. The polymerase chain reaction and low stringency library screening were used to isolate a rat genomic clone encoding a new dopamine receptor. Sequence data and pharmacological analysis reveal this clone is the rat analog of the human $D_4$ receptor, which exhibits a high affinity for the antipsychotic drug clozapine. The mRNA for this receptor shows a restricted pattern of expression in the central nervous system. Significant levels of expression were found in the hypothalamus, thalamus, olfactory bulb, and frontal cortex. However, 20-fold higher levels of $D_4$ mRNA expression were observed in the cardiovascular system. High levels are also expressed in the photoreceptor layer of the retina. Stimulation of this receptor in the dark leads to a marked decrease in the light sensitive pool of cAMP. Thus, this receptor appears to mediate dopamine function in the cardiovascular and retinal system as well as the central nervous system.

The creation of a transfected mouse fibroblast cell line that expresses a ligand-specific receptor with the pharmacological profile of a $D_2$ subtype has been reported by Todd et al., (1989) "Cloning of ligand-specific cell lines via gene transfer: identification of a $D_2$ dopamine receptor subtype" Proc. Natl. Acad. Sci. USA 86:10134–10138. As one strategy in the isolation of these sequences, a rat genomic library was screened with Tm-specific probes derived from $D_2$ (Bunzow et al., 1988) and $D_3$ (Sokoloff et al., 1990) consensus sequences. Using this approach, $D_1$, $D_2$, and $D_3$ rat genomic clones, as well as a clone of an unknown receptor that had a high degree of structural identity with $D_2$ and $D_3$ receptor genes, were identified. Sequence data and pharmacological analyses demonstrated that this was the rat equivalent of the human $D_4$ gene of Van Tol (1991), although significant differences, as shown below, exist between the human and the rat genes. The highest levels of expression of the rat analog of the human $D_4$ "clozapine" receptor are found in the heart and the proximal aortic arch.

EXAMPLE 1

Isolation and Characterization of the Rat $D_4$ Gene

The isolation and characterization of the gene and cDNA encoding the rat $D_4$ dopamine receptor will be further understood by reference to the following detailed description.

Materials and Methods

Isolation of the Rat $D_4$ Gene

A lambda Dash rat spleen genomic library (Stratagene) was screened for $D_2$-like receptor sequences with the use of radiolabeled Tm II, III, and VI/VII probes. Oligonucleotides encompassing the indicated domains were derived from consensus sequences from the rat $D_2$ (Bunzow et al., 1988) and $D_3$ genes (Sokoloff et al., 1990). Labeling of probes, hybridization, and washing were performed according to standard methodologies, for example, as described by Sambrook et al., (1989): Molecular Cloning: A Laboratory Manual. Cold Spring Harbor, N.Y., Cold Spring Harbor Laboratory; and Feinberg and Vogelstein, (1984) "A technique for radiolabeling DNA restriction endonuclease fragments to high specific activity" Anal. Biochem. 137:266–267. Hybridization-positive clones were further characterized by amplification using the polymerase chain reaction (PCR) with gene-specific probes derived from coding and intron sequences of the rat $D_2$ gene (O'Malley et al., (1990) "Organization and expression of the rat $D2_A$ receptor gene: identification of alternative transcripts and a variant donor splice site" Biochemistry 29:1367–1371), the rat $D_3$ gene (Sokoloff et al., 1990), and the rat $D_1$ gene (Monsma et al., 1990). Hybridization-positive, PCR-negative clones were plaque purified and further characterized. A 3.8-kb BamHI fragment common to the seven clones that were Tm VI/VII-positive but not identified as $D_2$, $D_3$, or $D_1$, was subcloned and sequenced using the method of Chen and Seeburg (1985) "Supercoil sequencing: a fast and simple method for sequencing plasma DNA" DNA 4:165–170. DNA sequence analysis was performed with computer programs generated by Intelligenetics. The reported sequences are available from GenBank under accession number M84009.

The derived gene sequence for rat dopamine $D_4$ receptor is shown as Sequence ID No. 1. The deduced amino acid sequence is shown as Sequence ID No. 2.

Expression Vectors

A full-length $D2_{A444}$ cDNA clone (2.3 kb) was isolated from a rat striatal library and subcloned into the HindIII site of pcDNA/neo. A genomic $D_4$ fragment generated by partial NarI digestion and complete BamHI digestion was made blunt ended and ligated into the EcoRV site of pcDNA/neo. The $D_4$ gene in the expression vector started at nucleotide –5 and stopped 336 bp 3' of the stop codon. DNA was purified as described by Gandelman et al., (1990) "Species and regional differences in the expression of cell type specific elements at the human and rat tyrosine hydroxylase gene loci" J. Neurochem. 55:2149–2152, for transfection.

Cell Culture and Transfection

Mouse CCL1.3 tk⁻ fibroblasts were grown in DMEM media supplemented with 10% fetal bovine serum. Cells were plated at a density of 3×10⁶ cells/10–cm dish, 12 to 24 h prior to transfection. Each plate of cells was transfected with 20 µg of plasmid DNA by $CaPO_4$ precipitation, using the method of Chen and Okayama (1987) "High efficiency transformation of mammalian cells by plasmid DNA" Mol. Biol. 7:2745–2752. Four hours after transfection, cells were shocked with 20% glycerol in DMEM for 2 min, and 48 h later the cells were split and placed in fresh media supplemented with 400 µg/ml of G418 (Geneticin, Gibco, active concentration). After two weeks, G418-resistant colonies were isolated with micropipette tips and screened for expression of $D2_{A444}$ or $D_4$ mRNA by reverse transcription/PCR analysis. Subclones expressing high levels of $D2_{A444}$ or $D_4$ mRNA were expanded and further characterized.

Binding Studies

Mouse fibroblasts expressing $D2_{A444}$ and $D_4$ were grown to 70% confluence and then harvested by scraping. After they had been washed twice in PBS, the cell pellets were resuspended in distilled water and ruptured by homogenization with a Brinkman Polytron, at setting 6 for 10 sec. Nuclei were removed by centrifugation for 5 min at 600 g. Membranes were pelleted by centrifugation for 25 min at 50,000 g. The pellets were resuspended in water and frozen at –70° C. until assayed. For receptor binding assays, samples containing 150 µg of membrane protein were aliquoted into glass test tubes. [³H]-Spiperone (1 nm) and varying concentrations of competing compounds were added in a final volume of 1 ml and a final buffer of 1.5 Mm $CaCl_2$, 5 mM $MgCl_2$, 5 mM KCl, 120 mM NaCl, 50 mM Tris-HCl, pH 7.4 at 20° C. The tubes were incubated for 15 min at 37° C., and the assays were terminated by addition of 5 ml of ice-cold 50 Mm Tris-HCl buffer (pH 6.9), collected onto glass-fiber filters, and washed twice with the same cold buffer in a modified Brandel cell harvester. The radioactivity retained on the filters was counted in a Beckman LS 1701 scintillation counter.

Oligonucleotides

Oligonucleotide primers were synthesized on an Applied Biosystems synthesizer. The Tm VI/VII primer set included orD-403, 5'-TGCTGGCTGCCCTTCTTC-3' (Sequence ID No. 5), which is identical to sequences within Tm VI in both $D_2$ and $D_3$ genes, and orD-404, 5'-GAAGCCTT-GCGGAACTC-3' (Sequence ID No. 6), which is complementary to sequences from TM VII. For tissue distribution studies total RNA was reverse transcribed using $orD_4$-515, 5'-CTGTCCACGCTGATGGCG-3' (Sequence ID No. 7), which is complementary to nucleotides 366 to 383 shown in Sequence ID No. 1. Second strand synthesis and further amplification utilized $orD_4$-465 and $orD_4$-466, 5'CAGACACCGACCAACTA-3' (Sequence ID No. 8), which is identical to nucleotides 187 to 204. Additional oligonucleotides included $orD_4$-474. 5'-TGACA-CCCTCATGGCCAT-3' (Sequence ID No. 9), which is identical to nucleotides 309 to 326; $orD_4$-465, 5'-TTGAAGATGGAGGGGGTG-3' (Sequence ID No. 10), which is complementary to nucleotides 342 to 359; $orD_4$-501, 5'-GCACACCAAGCTTCACAG-3' (Sequence ID No. 11), which is identical to nucleotides 657 to 674; and $orD_4$-506, 5'-TTGAAGGGCACTGT-TGACATAGC-3' (Sequence ID No. 12), which is complimentary to nucleotides 1064 to 1085. Oligonucleotides used for in situ hybridization included orD-502, 5'-ATGGTGTT-GGCAGGGAAC-TCGCTC-3' (Sequence ID No. 13), which is identical with nucleotides 124 to 193, and orD-499, 5'-GAGCGAGTTCCCTGCCAACACCAT-3' (Sequence ID No. 14), which is complementary to the same nucleotides.

mRNA Analysis by PCR

Total RNA was isolated from various tissues using the method of Chomczynski and Sacchi (1987) "Single-step method of RNA isolation by acid guanidium thiocyanate-phenol-chloroform extraction" Anal. Biochem. 162:156–159, reverse transcribed using the method of Krug and Berger (1987) "First-strand cDNA synthesis primed with oligo(dT)" Methods Enzymol. 152:316–325, and further amplified as described by O'Malley et al. (1990). Amplification temperatures were: denaturation at 93° C. for 1 min, annealing at 52° C. for 1 min, and synthesis at 72° C. for 1 min for 30 cycles. PCR products were transferred to nylon after electrophoresis in 5% polyacrylamide gels. Filters were probed with an end-labeled oligonucleotide, $orD_4$-474, corresponding to sequences that are internal to the amplification set. Filters were hybridized and washed according to the manufacturer's protocol (Schleicher and Schuell). The mRNA levels were normalized for equal amounts of the 18S fragment of ribosomal RNA by Northern blotting followed by hybridization with an 18S gene fragment, using the method of Chan et al., (1984) "The nucleotide sequence of a rat 18S ribosomal ribonucleic acid gene, and a proposal for the secondary structure of 18S ribonucleic acid" J. Biol Chem 259:224–230.

In Situ Hybridization

Sense and antisense $D_4$ oligonucleotide probes were end-labeled with digoxigenin-derivatized dUTP according to the manufacturer's protocols (Boehringer-Mannheim). Hybridization conditions were essentially as described by Springer et al., (1991) "Non-radioactive detection of nerve growth factor receptor. (NGFR) mRNA in rat brain using in situ hybridization histochemistry" *J. Histochem. Cytochem.* 39:231–234. The probe concentration was 35 ng/ml, and hybridization was overnight at 37° C. The final stringency wash was 0.5×SSC, 22° C. for 30 min.

Results

Low stringency screening of genomic libraries with Tm-specific probes was performed in order to isolate additional members of the dopamine $D_2$ receptor family. Because there are regions of very high identity between $D_2$ and $D_3$, notably within Tm domains II and III (100% amino acid identity) and TM VI and VII (70% and 87% amino acid identity, respectively), it was reasoned that DNA fragments specific for the region encoding each transmembrane sequence might be useful in identifying other members of the $D_2$-like receptor family. In addition, a comparison of the structure of the rat $D_2$ gene (O'Malley et al., 1990) with that of the $D_3$ gene (Sokoloff et al., 1990; Giros et al., (1991) "Shorter variants of the $D_3$ dopamine receptor produced through various patterns of alternative splicing. *Biochem. Biophys. Res. Commun.* 176:1584–1592) indicated a high degree of conservation in the intron-exon boundaries of these genes. Therefore, Tm specific probes were constructed so as to not cross these sites, so that genomic DNA could be used as a template. Domain-specific oligonucleotides were synthesized and DNA amplification methodology used to create double-stranded DNA starting with rat genomic DNA as a template. Fragments of the appropriate size were gel purified, radiolabeled, and hybridized to a rat genomic library. The number of phage screened corresponded to 15 rat genomes of inserted DNA.

The results of screening the same set of filters successively with the Tm II, III, and VI/VII probes are shown in Table 1.

TABLE 1

Results of screening a rat genomic library with degenerate oligonucleotides encompassing transmembrane domains II, III, and VI/VII.

| | Number of clones of each type identified by PCR* | | | |
|---|---|---|---|---|
| Probe | D1 | D2 | D3 | D4 |
| TM II | 13 | 38 | 24 | 0 |
| TM III | 7 | 43 | 20 | 0 |
| TM VI/VII | 0 | 21 | 25 | 7 |

*The receptor types of hybridization-positive plaques were identified with the use of gene-specific oligonucleotides in combination with PCR.

The feasibility of the strategy is evident from the detection of $D_1$ and $D_3$ using the indicated probes. No unknown dopamine receptors were detected with the Tm II and III probes, suggesting either that additional receptors have less identity in these domains or that these probes are too biased towards $D_2/D_3$ sequences. Probes to Tm domains I, IV, and V were not made, since there is only limited identity between $D_2$ and $D_3$ in these regions and no conservation of splice boundaries. Instead, the library was screened with the Tm VI/II probe. The majority of the 53 positive clones were $D_2$ and $D_3$. However, seven clones were clearly different and were further characterized. DNA from the seven isolates was digested with several restriction enzymes, blotted, and probed with the TM VI/VII probe. The smallest hybridizing fragment was subcloned into Bluescript and sequenced with the Tm VI/VII PCR primers.

Translated sequences revealed two hydrophobic domains that had 62% and 64% identity to $D_2$ and $D_3$, respectively, as well as a splice site in exactly the same position as in these genes, as described by Sokoloff et al., 1990; and O'Malley et al., (1990). Specific primers were designed from this sequence and used in unsuccessful screens of several cDNA libraries by the polymerase chain reaction (PCR), including libraries prepared from basal ganglia, hypothalamus, fetal brain, and pituitary. Subsequently, a battery of $D_2$ and $D_3$ primers derived from Tm domains I through V against the $D_4$ genomic clone were tested. They all seemed to hybridize to the same 3.8-kb BamHI fragment containing Tm regions VI and VII, suggesting that the new gene was very small in comparison with $D_2$ and $D_3$. Further sequence data confirmed this premise, revealing an overall gene structure of four exons and three introns spanning approximately 3500 bp, as shown in FIG. 1B and Sequence I.D. No. 1.

Comparison of the structural features and nucleotide sequence of the human $D_4$ receptor (Sequence ID No. 3, nucleotide sequence, and 4, deduced amino acid sequence) isolated from a human neuroblastoma cell line, as described by Van Tol and coworkers (1991), indicated that the new receptor is the rat analog of the $D_4$ receptor. The pharmacological profile of the human clone has confirmed its $D_2$-like nature and suggested that this receptor has a very high affinity for clozapine (5- to 15-fold higher than the $D_2$ receptor; Bunzow et al., (1988); Van Tol et al., 1991).

In the coding regions, the rat gene (Sequence ID No 1) shares 73% amino acid and 77% nucleic acid sequence homology with the human $D_4$ gene (Sequence ID No 3). In contrast, the rat and human $D_2$ receptors share 95% amino acid and 90% nucleic acid identity (Mack et al., (1991) "The mouse dopamine $D2_A$ receptor gene: sequence homology with the rat and human genes and expression of alternative transcripts" J. Neurochem. 57:795–801). As shown in FIG. 2, there is between 89% and 96% identity within the transmembrane domains of these genes. Most of the differences between rat and human $D_4$ genes occur in the third intracytoplasmic loop where there is only 50% amino acid identity. In the human, this region encompasses an unusual splice junction within intron 3 of the $D_4$ gene: instead of a canonical GT/AG donor/acceptor site, a TC/CT is indicated, as reported by Van Tol et al., (1991). This unconventional splice site is not observed in the rat gene. Subsequently, Van Tol et al., (1992) have modified their interpretation of the human D4 gene structure. The human and rat genes are now predicted to have the same number of introns and exons.

Figure 3A:
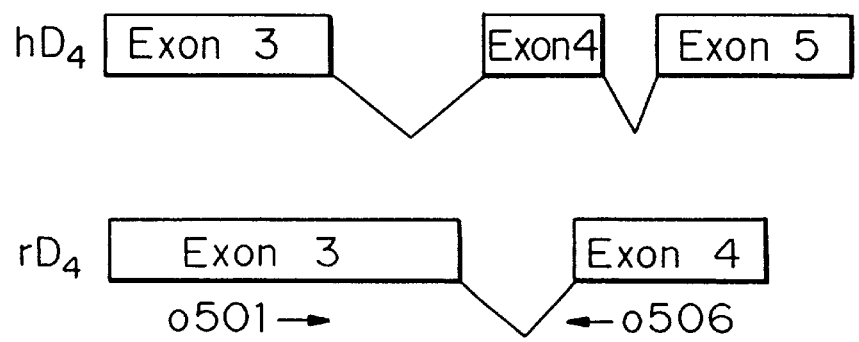
FIG. 3 is a comparison the structure of the Human $D_4$ receptor gene, which originally was reported to have an additional splice site, with the predicted structure of the rat $D_4$ gene. Oligonucleotides used for reverse transcription/PCR amplification are indicated. (B) Sequence of the cDNA generated by PCR amplification of reverse-transcribed rat atrial mRNA as described in the text. Identity and direction of the sequencing primers are indicated. Double lines to the right of the sequence indicate regions of identity with the human $D_4$ receptor sequence; thick lines demarcate transmembrane domains; the single line denotes non-identity of sequences between rat and human genes within the third cytoplasmic loop. The analogous location of the human exon 3/exon4 splice site is marked with an asterisk. The Tm VI splice site, which is conserved in all $D_2$-like receptors isolated to date, is indicated by an arrowhead.
Figure 3B:
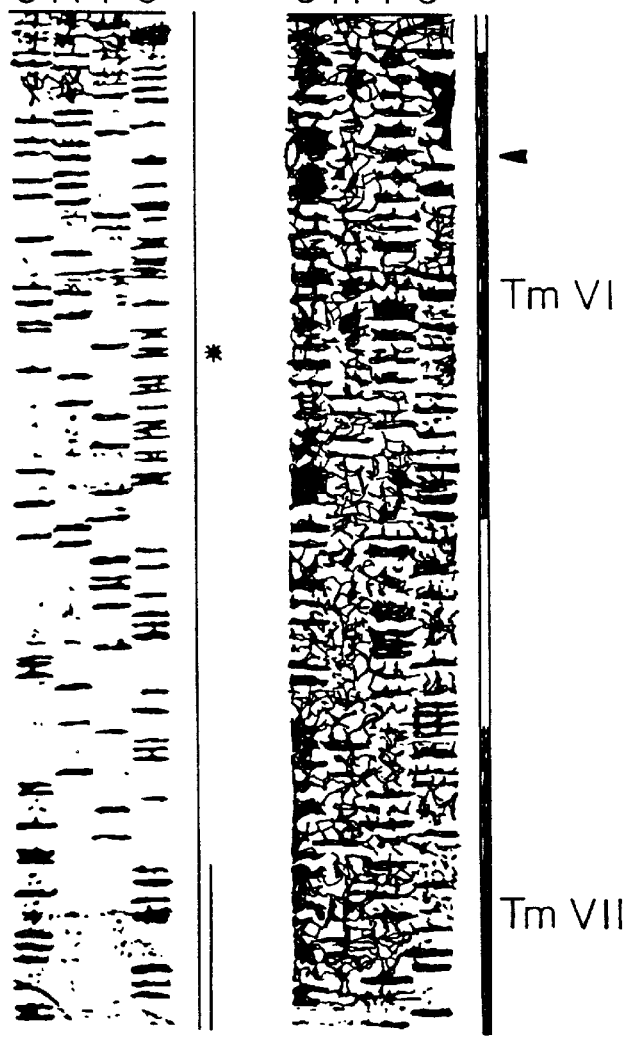

The strategy depicted in FIG. 3A was used in order to rule out the presence of a small intron, less than 30 bp, with a different unusual splice site. Oligonucleotides were chosen flanking the bona fide slice site within Tm VI (o506) and the putative splice site within the third cytoplasmic loop (o501). Amplification of genomic DNA would result in a 618-bp fragment when these primers are used. The proposed model of the rat $D_4$ gene predicts a 426-bp band for the cDNA. Rat atrial RNA was reverse transcribed with the use of primer o506, then PCR amplification was performed with the 501/506 primer set. A single band of 426 bp was obtained, which was subcloned and sequenced. FIG. 3B demonstrates the presence of the Tm VI splice site and the absence of any additional splice sites within this sequence. Therefore, the rat $D_4$ gene has four exons encoding an open reading frame of 368 amino acids.

EXAMPLE 2

Figure 4A:
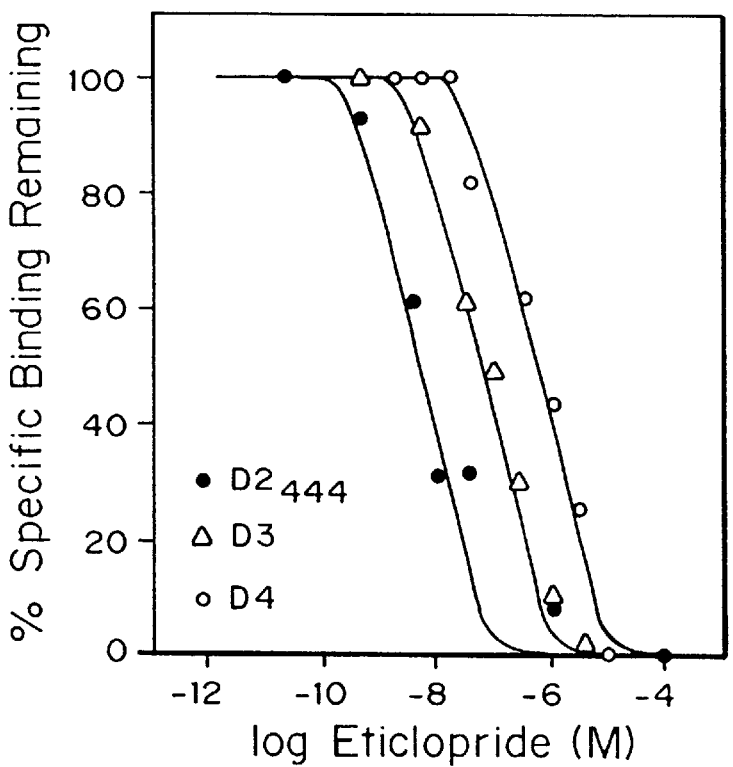
FIG. 4A is graph of [$^3$H]-spiperone (%) versus log [eticlopride, M].
Figure 4B:
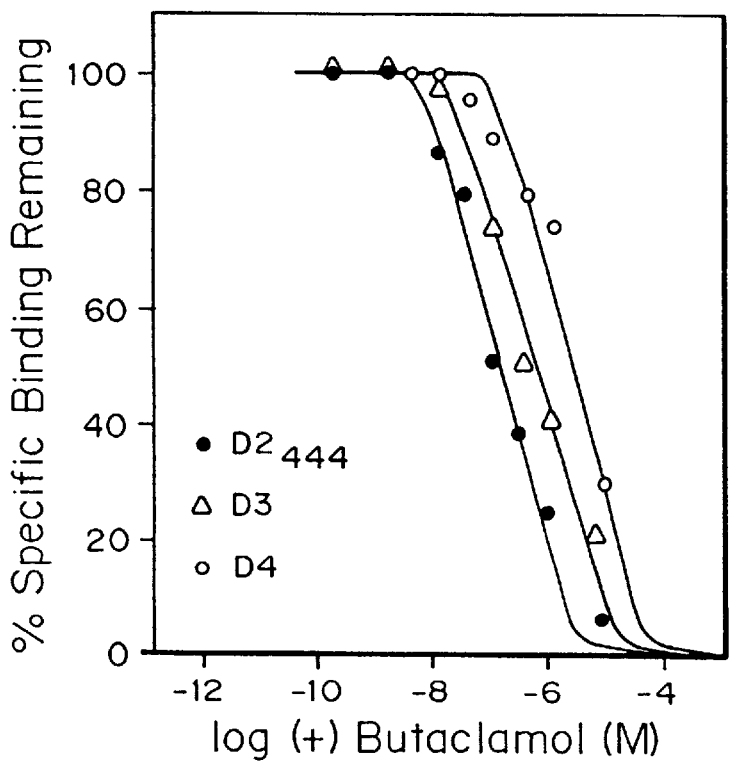
FIG. 4B is a graph of [$^3$H]-spiperone (%) versus log [(+)butaclamol, M].
Figure 4C:
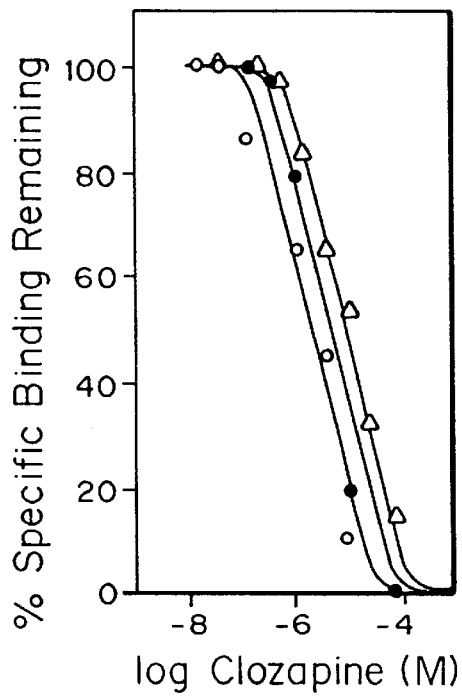
FIG. 4C is a graph of [$^3$H]-spiperone (%) versus-log [clozapine, M]. The rat $D_4$ gene, the rat $D_{2444}$ cDNA and the human $D_3$ cDNA were inserted into the expression vector pcDNA/neo and transfected into CCL1.3 cells. Subclones expressing the mRNAs were expanded in medium containing G418 and assayed for competition of 1 nM [$^3$H]spiperone binding by eticlopride, (+)butaclamal and clozapine, as described in Materials and Methods. Open circles, $D_4$-expressing cells; closed circles, $D_{2444}$-expressing cells, triangles, $D_3$-expressing cells. Results are shown as mean±SD of percent of specifically bound [$^3$H]spiperone remaining for an experiment done in triplicate. The apparent $K_i$'s for the $D_4$, $D_{2444}$ and $D_3$ receptors, respectively, were: 27.0±2.9 nM, 0.067±0.21 nM and 0.16±0.02 nM, for eticlopride, 51.3±17.5 nM, 0.69±0.15 nM; and 11.2±0.8 nM for(+) butaclamal; 41.7±6.1 nM, 142.5±4.3, and 620±51.6 nM for clozapine (mean±SEM for these experiments).

Pharmacological Confirmation that the Putative Rat $D_4$ Gene Codes for A $D_4$ Receptor To confirm that the putative rat $D_4$ gene codes for a dopamine receptor analogous to the human $D_4$ receptor, the rat gene was inserted into the expression vector pcDNA/neo and transfected into the CCL1.3 fibroblast cell line, which was then screened for [$^3$H]-spiperone binding. Transfected cells were enriched by expansion in medium containing G418. The rat $D_2$ cDNA and the human $D_3$ cDNA were expressed in the same cell line. The results of the [$^3$H]-spiperone binding studies are shown in FIGS. 4A, 4B, and 4C.

As determined by displacement with 1 $\mu$M eticlopride, specific binding of 2 nM [$^3$H]-spiperone was about 50% of the total bound counts for all three receptors. Similar to the results reported by Van Tol et al. for the human receptors, the rat $D_2$ receptor has a higher affinity for eticlopride and (+)butaclamol while the rat $D_4$ receptor has a 2- to 3-fold higher affinity for clozapine. The human $D_3$ receptor also has a higher affinity for eticlopride and (+) butaclamol and a much lower affinity for clozapine than the rat $D_4$ receptor. The relative rank order potency of these three compounds for the three receptors, however, demonstrates that the rat $D_4$ gene codes for a dopamine receptor analogous to the human $D_4$ gene.

Distribution of $D_4$ mRNA

Total RNA (250 $\mu$g) from the indicated regions was isolated, reverse transcribed, and amplified using primers flanking the first intron. PCR products were separated by electrophoresis, blotted onto nylon filters, and hybridized with an oligonucleotide internal to the PCR primers. Regions tested include adrenal medulla, adrenal cortex, occipital cortex, temporal/parietal cortex, frontal cortex, olfactory bulb, basal ganglia, hippocampus, medulla, thalamus, cerebellum, and mesencephalon. One microgram of hypothalamic total RNA and 250 ng of atrial and ventricle RNA were treated as described above, except that primer or D4-465 was used. This primer generates a 171-bp product.

Various CNS and peripheral tissues were examined for the presence and relative abundance of $D_4$ transcripts. Total RNA was reverse transcribed with a $D_4$ exon 2-specific primer, and this procedure was followed by second strand synthesis and DNA amplification. The predicted $D_4$ PCR product of 195 bp is detected in only a few central nervous system regions such as olfactory bulb, frontal cortex, and hypothalamus. Surprisingly, the $D_4$ PCR product is at least 20-fold more abundant in heart than in the CNS but is not detectable in liver, adrenal cortex, adrenal medulla, or kidney. Within the heart, $D_4$ is more abundant in the atrial/large vessel region. In separate experiments, mouse retinas were examined for the presence of $D_4$ transcripts and $D_4$ mRNA was found to be abundantly expressed in this tissue as well (Cohen, A. I., et al., (1992) "Photoreceptors of mouse retinas possess $D_4$ receptors coupled to adenylate cyclase" *Proc. Natl. Acad. Sci. USA* 89, 12093–12097).

To confirm and extend these results, digoxigenin-labeled oligonucleotide probes were used for in situ hybridization histochemistry. Sense and antisense oligonucleotides were end-labeled with digoxigenin-derivitized dUTP and hybridized to 20 $\mu$m frozen sections of heart and brain from 6- to 8-week-old male Sprague-Dawley rats. The hybridized oligonucleotides were visualized by alkaline phosphatase-linked anti-digoxigenin antisera and counterstained with eosin. Color development was for 16 h. Sections through the proximal aorta show intense staining of aorta. Color development was for 22 h. There was scattered hypothalamic staining in the region of the arcuate nucleus and the ventromedial nucleus of the hypothalamus, only a few positive cells in the striatum, no positive cells in the hippocampus, and the scattered presence of positive cells in the thalamus.

In the CNS, $D_4$ mRNA-positive cells were found primarily in hypothalamic areas surrounding the third ventricle. The hypothalamic distribution overlaps, but is not restricted to, the A11, A13, and A14 groups of hypothalamic dopaminergic cell bodies. Few positive cells were observed in the basal ganglia, hippocampus, or cortical regions. In the heart, heavily labeled cells predominated in the proximal aorta and the outflow tract of the left ventricle, with scattered positive cells throughout the central fibrous body. With more sensitive color development conditions, the predominant atrial expression of $D_4$ mRNA detected by PCR is evident. The distribution of staining is most consistent with the expression of $D_4$ mRNA in vascular smooth muscle and cardiac myocytes. $D_4$ mRNA was also identified in the retinal neuronal and photoreceptor layers in mouse (Cohen, et al., 1992).

The relatively high affinity of the human $D_4$ receptor for the neuroleptic drug clozapine, as reported by Van Tol et al., (1991), has generated interest in the possibility that this site is responsible for clozapine's novel antipsychotic effects. Clozapine also has significant tachycardia and hypotensive side effects. These have generally been ascribed to antagonist interactions at muscarinic acetylcholine receptor sites, as reported Fitton and Heel, (1990) "Clozapine. A review of its pharmacological properties, and therapeutic use in schizophrenia" *Drugs* 40:772–747. In the periphery, however, relatively selective $D_2$-like agonists, such as piribedil, can cause vasodilation, hypotension, and bradycardia, as reported by McCoy et al., (1986) "Selective antagonism of the hypotensive effects of dopamine agonists in spontaneously hypertensive rats" *Hypertension* 8:298–302. These effects appear to be due at least in part to inhibition of sympathetic nerve activity, Hohli et al., (1989), and can be blocked by peripheral $D_2$-like antagonists such as domperidone. Within the heart, $D_2$-like receptor stimulation has positive inotropic effects, Zhao et al., (1990) "Effects of dopamine $D_1$ and dopamine $D_2$ receptor agonists on coronary and peripheral hemodynamics" *Eur. J. Pharmacol.* 190:193–202. The demonstration of high levels of expression of $D_4$ mRNA in the cardiovascular system indicates that some of these effects may be secondary consequences of binding to peripheral $D_4$ Dopamine receptors and that clozapine may be a prototypic model for a new class of receptor-selective agents for the treatment of cardiovascular disorders. Of particular interest is the recent mapping of the locus for a familial form of the long Q-T syndrome to the vicinity of H-ras-1 on chromosome 11p, as reported by Keating et al., "Linkage of a cardiac-arrhythmia, the long QT syndrome, and the Harvey Ras-1 gene" *Science* 252:704–706 (1991). This is also the location of the human $D_4$ receptor gene, as reported by Gelernter et al., "DrD4, the $D_4$ dopamine receptor, maps to distal 11p" *Am. J. Hum. Gen.* 49:340 (1991). It is possible that an abnormality of the $D_4$ receptor may be responsible for this cardiac conduction disorder.

In summary, it was found that the rat $D_4$ receptor mRNA was expressed at low levels in several central nervous system regions but at much higher levels in the heart and retina. In situ hybridization studies are consistent with a hypothalamic autoreceptor function for the $D_4$ receptor in the central nervous system. The major site of expression, however, was in atrial and vascular myocytes. Therefore, the $D_4$ receptor, unlike the other $D_2$-like subtypes, may be predominantly a peripheral dopaminergic receptor. Accordingly, this receptor should be useful as a specific receptor for dopamine antagonists such as clozapine as well as dopamine agonists. By virtue of this specificity, many of these compounds can be used as regulators of blood pressure and heart rate. Depending on whether such compounds are agonists or antagonists, blood pressure may be raised or lowered and heart rate slowed or quickened. In addition, such compounds would increase or decrease, respectively, the efficiency of cardiac contractions (i.e., positive or negative inotropic effects). Similarly, such agonists and antagonists would decrease or increase light-sensitive pools of cAMP in retinal photoreceptors and effect the functioning of the eye. Effective dosages are determined based on the known dosages for these compounds for treatment of other disorders, screening for binding to cells expressing $D_4$ receptors, extrapolation to treatment of specific conditions, and other techniques known to those skilled in the art.

EXAMPLE 3

Morphogenic Potentials of D2, D3, and D4 Receptors

As discussed above, molecular cloning studies have defined a family of dopamine $D_2$-like receptors ($D_2$, $D_3$, $D_4$), which are the products of separate genes. Stimulation of dopamine $D_2$-like receptors in cultures of fetal cortical neurons increases the extension and branching of neurites (Todd, R. D. (1992) Biol. Psych 31, 794–807). To determine which $D_2$-like receptors possess morphogenic potentials, a clonal mesencephalic cell line (MN9D) was transfected with $D_2$, $D_3$, or $D_4$ receptor subtypes, treated with the $D_2$ agonist quinpirole, and changes in morphology quantitated.

The results demonstrated that stimulation of $D_2$ receptors increased the number and branching of neurites, with little effect on neurite extension, while stimulation of $D_3$ and $D_4$ receptors increased the branching and extension of neurites. These effects on neuronal morphology could be blocked by the dopamine $D_2$-like receptor antagonist eticlopride. These results suggest that all of the known $D_2$-like receptors may have specific developmental roles in regulating neuronal morphogenesis of dopaminergic pathways. The types of morphological effects seen suggest that developmental abnormalities of stimulation of these receptor subtypes may result in the neuroanatomical changes found in many neurological and psychiatric disorders such as mental retardation syndromes, schizophrenia, affective disorders and autism. Regulation of receptor subtype stimulation by agonists or antagonists during pre- or postnatal life may therefore be an effective form of treatment to prevent or reverse the development of anatomical abnormalities and these diseases.

Methods

Transfection

Different dopamine receptor cDNAs or genes were transfected into the dopamine containing mesencephalic cell line, MN9D. MN9D is a cell line produced by fusion of fetal mouse mesencephalic cells with N18TG2 neuroblastoma cells, described by Choi, H., et al. (1991) Brain Res. 552, 67–76. The MN9D cell line is a stable immortalized clonal cell line established by fusion of the neuroblastoma cell N18TG2 with embryonic mouse mesencephalic dopamine producing neurons. Some of the characteristics of these cells include: the synthesis and release of dopamine; neurite formation and immunoreactivity; production of large voltage-sensitive sodium currents generated by depolarization; sensitivity to MPTP, a dopaminergic neurotoxin, and the ability to distinguish between the presence of dopaminergic target and non-target cells. Additionally, neither the MN9D nor the CCL1.3 cell lines have detectable mRNA or expressed protein for any of the $D_1$-like or $D_2$-like receptors.

The exon 6 containing form of the rat D2 receptor ($D2_{444}$) (O'Malley, et al., "Organization and Expression of the rat $D_{2A}$ receptor gene: identification of alternative transcripts and a variant donor splice site" Biochem. 29:1367–1371 (1990)) (Sequence ID No. 15) and the human D3 receptor cDNA (Giros, et al., C.R. Acad. Sci. (Paris) III, 311, 501–508 (1990)) (Sequence ID No. 16) were inserted into the mammalian expression vector pcDNA/neo (Invitrogen). The entire rat D4 (Sequence ID No. 1) receptor gene was inserted into the same vector. All three plasmids were transfected into MN9D cells using the glycerol shock/calcium phosphate technique of Wigler, M., et al. (1979) Cell 16, 777–786; and Graham, F. and van der Eb, A (1973) Virology 52, 456–467, and permanent, clonal transfectants selected by G-418 resistance and limiting dilution. The clonal cell lines were assayed for expression of receptor mRNAs by reverse transcription of total cellular RNA with receptor specific oligonucleotides, followed by DNA amplification (O'Malley, K. L., et al, 1990) (RT/PCR) and for receptor protein by [$^3$H]-spiperone binding (Todd, R. D., et al, 1989). Each clonal cell line expressed only the transfected dopamine receptor mRNA and the expressed receptor proteins displayed the predicted pharmacological differences for $D_2$, $D_3$, and $D_4$ receptors. The average number of expressed receptors per cell for the $D_{2444}$, $D_3$, and $D_4$ expressing cell lines were about 45,000, 15,000, and 3,500 respectively.

Morphology

The parental and transfected cell lines were plated at low density (8 cells/mm$^2$) onto poly(D-)lysine coated 35 mm culture dishes (Corning). The medium was Dubecco's Modified Eagle's Media (Gibco) containing 10% fetal bovine serum. 0.05% (w/v) G-418, an antibiotic which selects for the transfected cells, was added to the medium for selection. The cells were cultured in a humidified incubator under 10% $CO_2$ with or without 1–2 $\mu$M quinpirole, a non-toxic D2-like receptor agonist.

To determine whether the stimulatory effects of quinpirole on neurite outgrowth could be blocked if mediated by dopamine $D_2$-like receptors, cells were co-cultured with 2 $\mu$M quinpirole and 1 $\mu$M eticlopride, a $D_2$-like receptor antagonist. $K_i$s (nM) for quinpirole are 4700±82 ($D2_{444}$), 1567±247 (D3), 453,3±71.0 (D4); $K_i$s(nM) for eticlopride 0.029±0.004 ($D2_{444}$), 0.46±0.12 (D3) 22.3±1.9 (all values are mean±SEM of triplicate determinations for three to five individual assays).

Based on the $K_i$ values, the micromolar concentrations of both quinpirole and eticlopride were expected to have stimulatory or inhibitory effects at each of the $D_2$-like receptors, respectively.

Cells were plated at low density, cultured overnight without treatment, then drugs or medium were added to the cultures. Quinpirole was added every 12 hours since this reagent quickly oxidizes. Eticlopride was added every 24 hours, and the control cultures received an equal amount of medium at the same time as the quinpirole additions. Living cells were photographed after 90 to 115 hours in culture using phase contrast microscopy (Nikon Diaphot) or a digital image processing system (Image-1). Morphologies of individual cells were quantitated at 1600× using a computer-interfaced drawing system with a digitizing light pad (Bioquant) as described by Todd, 1992; Sikich, L., Hickok, J. M., and Todd, R. D. Dev. Brain Res. 56, 269–274, 1990). Cells were measured consecutively over two to three dishes without knowledge of the treatment condition. Processes shorter than 5 µm were not reliably remeasured and were excluded from morphometric analysis.

Results

Transfection and subsequent agonist stimulation of dopamine $D2_{A444}$, $D_3$, and $D_4$ receptors in MN9D cells results in distinct changes in cell morphology. These persist for at least seven days in culture and can be blocked by dopamine D2-like antagonists.

Transfection Alters MN9D Morphology

The MN9D parent cell line which does not express either $D_1$- or $D_2$-like receptors, and the transfected cells lines expressing $D2_{A444}$, $D_3$ and $D_4$ receptors, elaborate neurites in culture. Unstimulated cells can be distinguished from one another less than 12 hours after plating and all the cell lines continue to develop in morphologically distinct manners for at least two weeks in culture. As shown for a single experiment in Table 2 (minus quinpirole), $D2_{A444}$ expressing cells tend to have more neurites and a larger neuritic extent. $D_3$ expressing cells have marked increases in neurite number, branch number and total neuritic extent, and $D_4$ expressing cells most closely resemble the parent MN9D cell line.

The cells were cultured with or without 2 µM quinpirole for 91–93 hours, photographed, and morphologies quantitated. All measurements were made without knowledge of the treatment condition and are expressed as means±SEM. In these analyses only neurites and neurite branches longer than 5 µM were included because of poor interrater reliability at shorter lengths. Statistical comparisons are shown for the effects of quinpirole on each individual cell lines. Since not all morphological characteristics were normally distributed all statistical analyses were non-parametric and are corrected for the number of comparisons. Significant differences from no added quinpirole condition (Mann-Whitney U test): ° $p<10^{-2}$; $^{108}$ $p<10^{-3}$; $^+p<10^{-4}$; $^\dagger p<10^{-5}$; $^\ddagger<10^{-6}$. MANOVA post hoc comparisons of morphological characteristics between cell lines are shown in Table 3.

TABLE 3

Comparisons of neurite outgrowth between the transfected cell lines and the MN9D parent cells.

| | Parameter | Comparison | p value |
|---|---|---|---|
| Control | Neurite Number | MN9D/MN9D3 | .008 |

TABLE 3-continued

Comparisons of neurite outgrowth between the transfected cell lines and the MN9D parent cells.

| | Parameter | Comparison | p value |
|---|---|---|---|
| | Branch Number | MN9D/MN9D3 | .004 |
| | | MN9D2/MN9D3 | .003 |
| | | MN9D3/MN9D4 | $<10^{-3}$ |
| Ouinpirole | Branch Number | MN9D/MN9D2 | $<10^{-3}$ |
| | | MN9D/MN9D3 | $<10^{-6}$ |
| | | MN9D/MN9D4 | .002 |
| | | MN9D3/MN9D4 | .020 |
| | Primary Neurite Length (µm) | MN9D/MN9D3 | $<10^{-3}$ |
| | | MN9D/MN9D4 | $<10^{-4}$ |
| | | MN9D2/MN9D3 | .011 |
| | | MN9D2/MN9D4 | $<10^{-4}$ |
| | Total Neuritic Extent (µm) | MN9D/MN9D2 | .035 |
| | | MN9D/MN9D3 | $<10^{-6}$ |
| | | MN9D/MN9D4 | $<10^{-5}$ |
| | | MN9D2/MN9D4 | $<10^{-4}$ |

Quinpirole Enhances Morphological Changes in Transfected Cells

The transfected dopamine D2-like receptor expressing cell lines have distinct morphologies. Since the parent

TABLE 2

Effect of Quinpirole on Cell Morphology

| | Transfected MN9D Cells | | | | | | | |
|---|---|---|---|---|---|---|---|---|
| | MN9D | | $D2_{A444}$ | | D3 | | D4 | |
| Quinpirole | − | + | − | + | − | + | − | + |
| Number of Cells | 100 | 100 | 100 | 100 | 59 | 59 | 100 | 100 |
| Neurite Number per Cell (µm) | 3.25 ± .21 | 4.25 ± .23$^{\#*}$ | 3.98 ± .21 | 4.72 ± .23 | 4.45 ± .29 | 4.64 ± .26 | 3.73 ± .23 | 4.12 ± .23 |
| Branch Number per cell (µm) | .69 ± .16 | .63 ± .12 | .66 ± .15 | 2.35 ± .35$^\S$ | 1.91 ± .35 | 3.51 ± .34$^+$ | .51 ± .17 | 2.10 ± .29$^\dagger$ |
| Primary Neuritic Length (µm) | 24.54 ± 2.07 | 22.94 ± 2.01 | 31.30 ± 6.21 | 30.09 ± 2.02 | 32.50 ± 5.90 | 54.24 ± 6.69$^\dagger$ | 21.56 ± 1.62 | 59.82 ± 6.7$^\ddagger$ |
| Total Neuritic Length (µm) | 59.75 ± 5.74 | 63.29 ± 4.39 | 78.22 ± 9.62 | 104.48 ± 8.95* | 96.10 ± 12.34 | 157.77 ± 13.94$^+$ | 58.00 ± 5.43 | 140.53 ± 13.56$^\ddagger$ |

MN9D cell line synthesizes and releases dopamine (Choi, H. K. Won, L. A., Kontur, L. A., et al, (1991) *Brain Res.* 552, 67–76) these differences may be secondary to autostimulation of the expressed receptors by release of endogenous dopamine. To test whether further stimulation of receptors would result in increased morphological differences, cells were cultured in the presence of the dopamine $D_2$-like agonist quinpirole. This agonist was chosen for its high affinity for all three receptors and its low toxicity to neuronal cells.

Figure 5A:
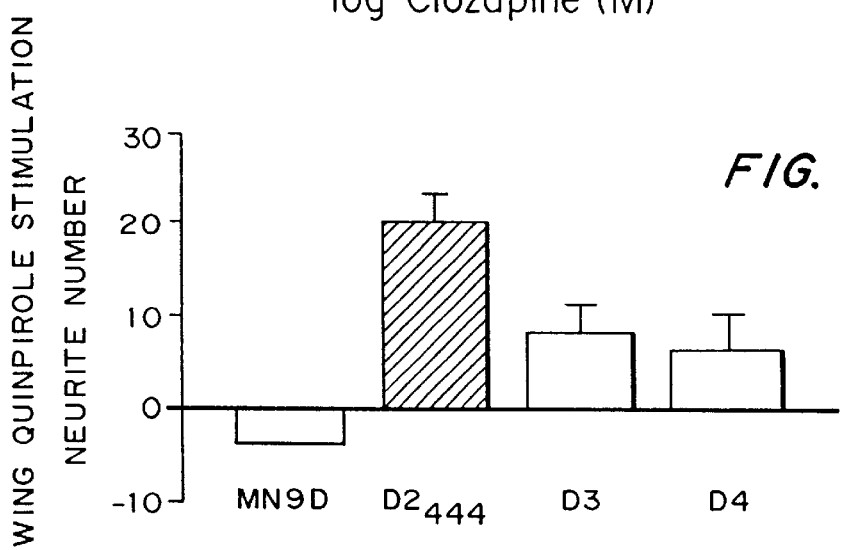
FIGS. 5A, B, C and D, are bar graphs of neurite number (FIG. 5A), branch number (FIG. 5B), primary neurite length (FIG. 5C), and total neurite extent (FIG. 5D), in percent change following quinpirole stimulation for control MN9D cells, and $D2_{444}$, $D_3$, and $D_4$ transfected cells. The data of three separate experiments for each of the four cell types are expressed as the average percent change±SEM from control (unstimulated) cells. Cell numbers for the individual experiments were 100 for each condition except for one experiment each for the D3 and D4 receptor expressing cells, in which there were 59 and 38 cells for each condition respectively. The cells were plated at low density and cultured for 90 to 95 hours with or without 1 to 2 μM quinpirole. Significant changes are indicated by filled bars. Open bars represent non-significant changes.

Culture with quinpirole resulted in increased morphological differences between the transfected and parent cell lines. Differences between cell lines were apparent within 24 hours of exposure to quinpirole and lasted for at least 115 hours. Table 2 shows the results of a single experiment in which MN9D parent cells and the cell lines transfected with $D2_{A444}$, $D_3$ and $D_4$ receptors were cultured for 91 to 93 hours with and without 2 µM quinpirole. Compared to MN9D cells, stimulation of the transfected cell lines with quinpirole resulted in significant increases in the number of branches and extension of neurites (Table 3). Stimulation of $D2_{A444}$ receptors resulted in a four fold increase in the frequency of branching of neurites with little effect on neurite extension (n=100 cells for each condition, significance levels given in Table 3). $D_3$ receptor stimulation resulted in increases in neurite branching and neurite length (n=59 cells for each condition). $D_4$ receptor stimulation resulted in a small increase in neurite branching and a large increase in neurite extension (n=100 cells for each condition). These effects have been observed in three independent experiments for each receptor expressing cell line, as depicted in FIGS. 5A, B, C, and D. Treatment of the MN9D parent cells with 2 μM quinpirole resulted in no increases in neuritic outgrowth with the exception of the neurite number. As shown in Table 2, in this experiment there was a small but statistically significant increase in neurite number. However, in two other experiments, no significant differences in any morphological parameter were found on stimulation of MN9D cells (n=100 cells per condition for each experiment).

Figure 5B:
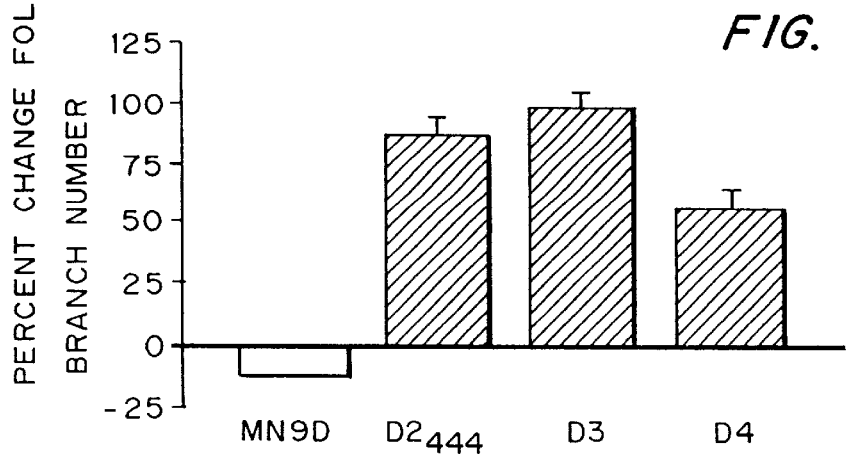
Figure 5C:
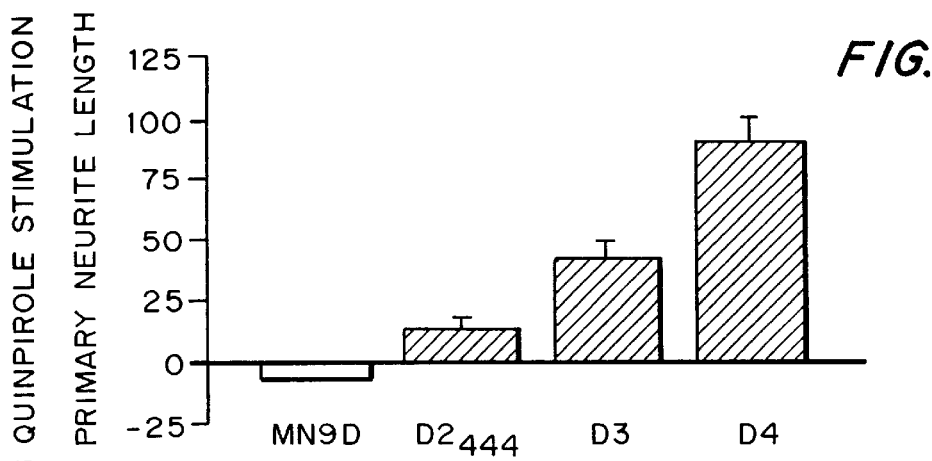
Figure 5D:
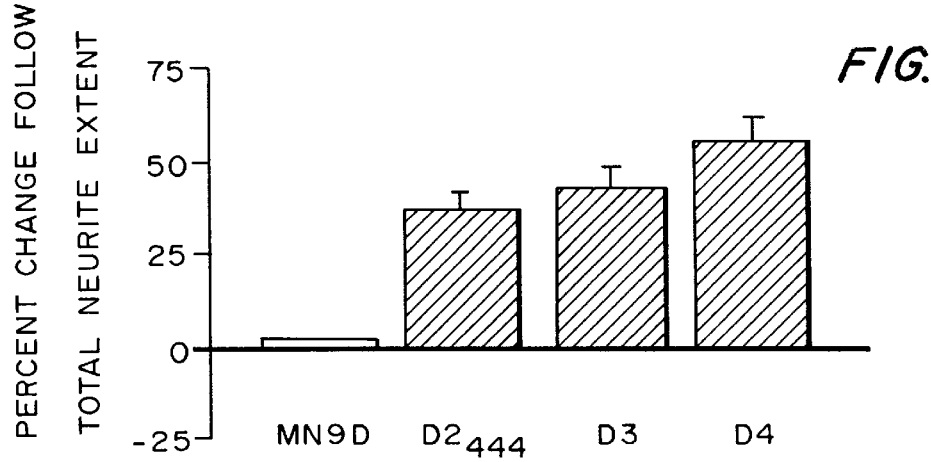

The effects of quinpirole stimulation varied with receptor subtype, as compared to the unstimulated state of each cell line. As shown in FIGS. 5A, 5B and 5C, $D2_{A444}$ stimulation resulted in significant percent increases in neurite number and branch number with only a small increase in neurite length. $D_4$ stimulation resulted in the largest percent increase in neurite length with no effect on neurite number. $D_3$ stimulation resulted in marked increases in branch number and neurite length with no effect on neurite number.

Figure 6:
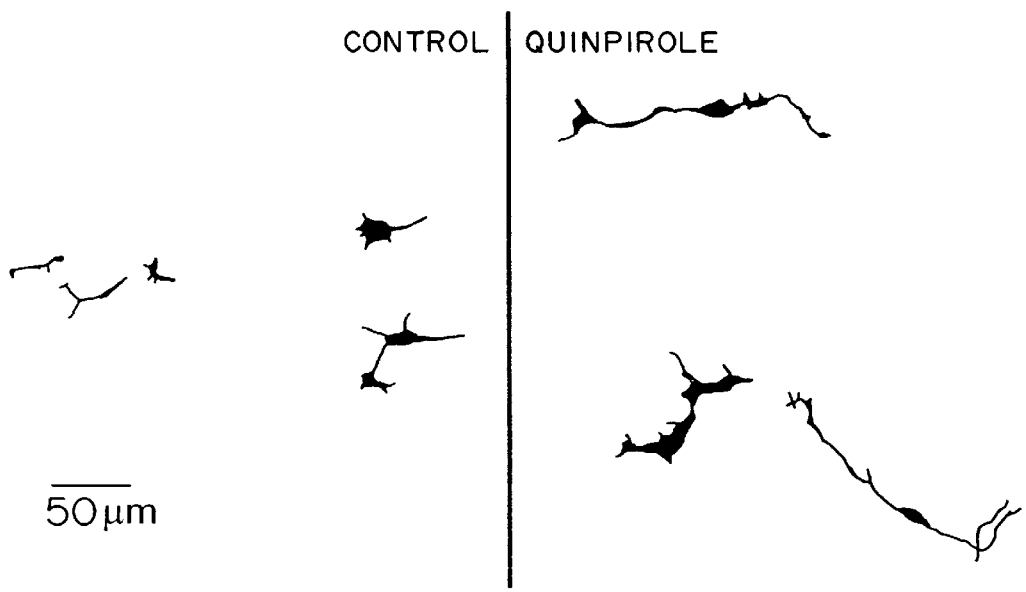
FIG. 6 is a comparison of control and quinpirole treated cells. Cells from E15 rat mesencephalon were plated at high density, incubated for 12 hours, and cultured for 90 hours in the presence (quinpirole) or absence (control) of 2 μM quinpirole. Cultures were then fixed and dopamine synthesizing cells identified by tyrosine hydroxylase immunoreactivity. Figure shows camera lucida drawings of tyrosine hydroxylase expressing cells in confluent cultures. There are five TH positive cells in the control condition and three TH positive cells in the quinpirole condition. In the presence of quinpirole TH positive cells were larger, have more branch points and much more extensive growth cone elaboration.

In summary, though the $D_3$ expressing MN9D cell line had more differentiated neurites in the unstimulated state, the $D_{2A44}$ expressing cell line showed a larger increase in neurite length following quinpirole stimulation. On average, as compared to untransfected MN9D cells, the morphological effects of transfection and stimulation are that $D2_{A444}$ expressing MN9D cells have more branched neurites while $D_4$ expressing cells have longer less branched neurites. Stimulated, $D_3$ expressing MN9D cells have the most highly branched neurites and the longest total neuritic extents. The effects of quinpirole stimulation of all three receptors can be blocked by 1 μM eticlopride. Similar results have been found for quinpirole stimulation of primary cultures of dopaminergic, mesencephalic neurons which express a mixture of receptor subtypes, as shown by FIG. 6.

In conclusion, dopamine $D_3$-like receptors transfected into a clonal mesencephalic cell line regulate neurite outgrowth in these cells and the $D_2$ receptor subtypes appear to modulate different aspects of neurite outgrowth. These results suggest a role for dopamine $D_2$-receptors in mammalian neurodevelopment and provide support for the possibility that dopamine receptor subtypes differentially modulate neurite outgrowth in vivo. The observation of similar effects on neurite outgrowth in primary mesencephalic cultures supports the relevance of these effects for normal and abnormal brain development.

Assuming these responses occur in vivo, then fundamental changes in the anatomy and function of mesocortical and mesostriatal pathways could occur via abnormal receptor stimulation. These are the same brain regions where neuropathological and neuroimaging abnormalities have been reported for disorders such as schizophrenia (Benes, F. M., Davidson, J. and Bird, E. D. (1986) *Arch. Gen. Psychiatr.* 43, 31–35; Jeste, D. V. and Lohr, J. B. (1989) *Arch. Gen. Psychiatr.* 46, 1019–1024; Pfefferbaum, A. et al. (1988) *Arch. Gen. Psychiatr.* 45, 633–640. The results also indicate that developmental stimulation or inhibition of dopamine receptor subtypes via drugs, both therapeutically and abusively, can result in profound pre- and postnatal changes in neuronal morphology and function. Developmental regulation of receptor stimulation therefore offers a therapeutic approach to preventing or reversing neuroanatomical changes associated with a variety of neurological and psychiatric diseases.

EXAMPLE 5

Use of the Rat $D_4$ as a Screen for Cardiovascular Drugs and Other Biologically Useful Compounds The cDNA or gene encoding the $D_4$ dopamine receptor can be expressed in a variety of mammalian cell lines, including the fibroblast cell line described above, or in other commercially available cell lines such as Cos cells, and used to screen for compounds which bind specifically to the $D_4$ receptor. This is determined by comparing binding affinities for the various $D_1$, $D_2$, and $D_3$ receptors with that of the $D_4$ receptor, then testing in vivo those compounds which specifically bind the receptor. It can also be expressed in bacterial cells, notably *E. coli*, as well as other eukaryotic expression system such as Baculovirus infection of insect cells.

Based on the discovery that the $D_4$ dopamine receptor is predominantly associated with cardiovascular and retinal tissues, a principle use for this screen is for compounds having an effect on the cardiovasculature and retina, either dopamine antagonists or dopamine agonists, that act as vasoregulators or have ionotropic effects and that act on retinal cyclic AMP levels. Compounds which bind either the human or the rat $D_4$ dopamine receptor can be screened. The typical models for physiological testing of these compounds are rats, mice and dogs. Measurements can be made in intact animals, in cardiovascular and retinal tissue explants or in isolated cells.

The gene and/or cDNA can also be used to generate probes for screening in a manner similar to those methods described above for receptors other than the known $D_1$, $D_2$, $D_3$, and $D_4$ dopamine receptors. Probes are created from sequences generally fourteen to seventeen nucleotides in length, and can be labelled using available technology and reagents, including radiolabels, dyes, tomography position emission labels, magnetic resonance imaging labels, enzymes, and fluorescent labels. Probes can be used directly or indirectly via standard methodologies including polymerase chain reaction (PCR) and methodologies to generate larger fragments of the D4 receptor. Starting with either RNA (via RT/PCR) or DNA, the D4 cDNA, and parts therein, can also be used to generate RNA transcripts if cloned into appropriate expression vectors (cRNAs).

D4 DNA fragments, oligonucleotide probes or cRNAs, could all be used in commercial kits or sold separately to measure D4 transcript levels using standard techniques including PCR, in situ hybridization, and RNAse or SI protection assays.

Amino acid sequences can be deduced from fragments of D4 DNA Sequence, or the entire D4 coding sequence, generated by a variety of standard techniques for synthesis of D4 synthetic peptides, D4 fusion proteins and/or purification of D4 proteins (or parts thereof) from in vitro translated proteins derived from synthetic D4 RNA or protein purification per se. D4 proteins, peptides, fusion proteins or fragments thereof could subsequently be used for antibody production using available technology including injection into a wide variety of species including mice, rats, rabbits, guinea pigs, goats, etc. for the production of polyclonal antisera as well as injection into mice and subsequent utilization of fusion techniques for the production of monoclonal antibodies.

Oligonucleotides or larger sequences derived from the D4 mRNA or complementary sequences or antibodies directed against the D4 receptor could be labelled or derivatized to be used as imaging agents for positron emission tomography (PET) or magnetic resonance imaging (MRI) of the location of D4 receptors in vivo and in vitro.

Promoter sequences associated with the rat D4 receptor (5' flanking sequences) may be utilized to create transgenic (non-human) animals via standard methodologies, for example, by microinjection into embryos or homologous recombination in embryonic stem cells. Depending upon the reporter gene utilized (Lac Z, diptheria toxin, etc.) various animal models can be created leading to the overexpression or loss of D4 receptor activity. Additionally, promoter sequences driving foreign gene products such as the SV40 large T antigen could be used to create immortalized cell lines from D4-expressing cell types. Selected use of other foreign reporter genes (e.g. cholera toxin) can be used to make model systems whereby central nervous system or peripheral physiology can be modified. Finally, from the sequence information presented in sequences 1 and 2, vectors can be generated for subsequent homologous recombination experiments in which the D4 gene is inactivated or "knocked out", allowing determination of the physiological role of the D4 gene.

Antibodies against the D4 receptor can be used for immunocytochemical localization, flow cytometry identification and isolation of D4 receptor expressing cells. Antibodies can also be used to block or modify the effects of D4 receptor agonists and antagonists both in vivo and in vitro.

The present invention is further understood by reference to the following nucleotide and amino acid sequences.

Sequence 1 is the nucleotide sequence for both the non-coding and protein coding regions of the rat D4 receptor gene loci.

Sequence 2 is the derived amino acid sequence for the rat D4 receptor protein.

Sequence 3 is the nucleotide sequence for the human D4 receptor cDNA.

Sequence 4 is the derived amino acid sequence for the human D4 receptor protein.

Sequences 5–14 are oligonucleotide primers used in the isolation of the rat D4 receptor gene.

Sequence 15 is the nucleotide sequence for the rat D2 receptor cDNA (444 amino acid form).

Sequence 16 is the nucleotide sequence for the human D3 receptor gene.

Modifications and variations of the present invention will be obvious to those skilled in the art from the foregoing detailed description. Such modifications and variations are intended to come within the scope of the following claims.

SEQUENCE LISTING (1) GENERAL INFORMATION:

(iii) NUMBER OF SEQUENCES: 16

(2) INFORMATION FOR SEQ ID NO:1:

(i) SEQUENCE CHARACTERISTICS:
      (A) LENGTH: 3907 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (iv) ANTI-SENSE: NO (vi) ORIGINAL SOURCE:
      (A) ORGANISM: Rattus norvegicus
      (F) TISSUE TYPE: Spleen genomic DNA (ix) FEATURE:
      (A) NAME/KEY: misc_feature
      (B) LOCATION: 1..3907
      (D) OTHER INFORMATION: /note= "Rat D4 Gene"

(ix) FEATURE:
      (A) NAME/KEY: misc_feature
      (B) LOCATION: 1..820
      (D) OTHER INFORMATION: /note= "5' flanking sequence to end
         of exon 1"

(ix) FEATURE:
      (A) NAME/KEY: intron
      (B) LOCATION: 821..2299

(ix) FEATURE:
      (A) NAME/KEY: exon
      (B) LOCATION: 2300..2406

(ix) FEATURE:

(A) NAME/KEY: intron
        (B) LOCATION: 2407..2499

(ix) FEATURE:
        (A) NAME/KEY: exon
        (B) LOCATION: 2500..3071

(ix) FEATURE:
        (A) NAME/KEY: intron
        (B) LOCATION: 3072..3263

(ix) FEATURE:
        (A) NAME/KEY: misc_feature
        (B) LOCATION: 3264..3907
        (D) OTHER INFORMATION: /note= "Exon 4 and 3' flanking
             sequence"

(ix) FEATURE:
        (A) NAME/KEY: misc_feature
        (B) LOCATION: 445..447
        (D) OTHER INFORMATION: /note= "Start codon (initiator
             methionine)"

(ix) FEATURE:
        (A) NAME/KEY: misc_feature
        (B) LOCATION: 3463..3465
        (D) OTHER INFORMATION: /note= "Stop codon (TGA)"

(x) PUBLICATION INFORMATION:
        (A) AUTHORS: O'Malley, K. L.
             Harmon, S.
             Tang, S.
             Todd, R. D.
        (B) TITLE: The rat dopamine D4 receptor: sequence, gene
             structure and demonstration of expression in the
             cardiovascular system.
        (C) JOURNAL: New Biol.
        (D) VOLUME: 4
        (F) PAGES: 1-9
        (G) DATE: 1992

(xi) SEQUENCE DESCRIPTION: SEQ ID NO:1:

```
GATCCCAAGC GTTGTTCCCT ATCTGCCCAT GCGTGGGTGT CGGATGAAGA GTGAGCTTGA      60

TGTGCCCGAT TGTTCAGTAT TGCTGAGCCT AGAACCCTTA GAGAAAGAGA GGAGGAGCCT     120

TAGCCTGTTA CAGAACCAGA GTTGATGGTT TCCTACGTGG AAGGACCCAA ATGCAGGAGT     180

CCAATAGTTC CACCACGTCC TCCAAGGTAT CTTGGAGAGA CGCTTTTGAC AAGCAATTTA     240

GTGGCCTGTC TCCTCGACGG GATGACTGAC TCTGACGAAT CTGGTCCAGA CAACCTGCTT     300

TCCATATAGT TTTCTGGAAG CACAAACTAA CCTGGATCAG GGGAAACATC AGTCGCTGCT     360

CCACCTTTTA TGCCAGTCAC TTTGCTCTTG AATTGAAGCA TTTCTCCCTC TGCCAATTTC     420

CTAGAGTGCA GAAATTCAAG CCGTGGCGGG CGGGGCGGAG CTGGACGCTG GGGCGGGAT      480

TCCGGATAGC CCCTGACTGC AAATCCCCAG GCTCAGCGCC TTGCAGAGTC TCAGCTAGGG     540

CGCCATGGGG AACAGCAGCG CTACTGGTGA CGGTGGGCTG TTGGCCGGGC GTGGGCCAGA     600

GTCCTTAGGT ACTGGCACCG GACTTGGGGG CGCGGGCGCG GCGGCGCTGG TGGGAGGCGT     660

GCTGCTCATC GGCATGGTGT TGGCAGGGAA CTCGCTCGTT TGCGTGAGCG TGGCCTCCGA     720

GCGCATCCTG CAGACACCCA CCAACTACTT CATCGTGAGC CTGGCGGCTG CCGACCTCCT     780

CCTCGCGGTG CTGGTGTTGC CTCTCTTTGT CTACTCCGAG GTGAGCCTCG GTGCACTCTT     840

TCCCTAGCTC CATGGCTCCC AGCACCCCAG CCCCAGCGCG GTTTCACGCT TAGACCCTCA     900

GCAACCTTGA GCCAGGGGGT TTGCAGGGAC GCCAGGTCTC CTCACTCCTG ACTACCCACT     960

TTCTCCCGCT CTTCAGAATC TTTCGCCTAC TTTTCCTCCG TCACCCTACC ATCCTCTGAA    1020

TCCCTTCCTA TTCTATCTAA GATCTGCCAA CCCAGAGAGG ACTCGTGTCC CTAAAACCAA    1080
```

```
GGATCACAGA AAAATGTCTT TCCTATTTAA GCCCTGGCTC CCACTGCAGA AATACTGCAC    1140

CCCCAGCCCC CGCCAAAAGC CTGCTAGACA GGCAGGCGAA TGTGCAGACA CACATCACTG    1200

CCAATGACCA CTGCCTTTTG GAACACACA CACACACACA CACACACACA CACACACACG    1260

CCAGCCTGTG CCAGCTCACC CTAAGGAAGA AGCCCCAAAG CCCGCAGCCA CCCAGATGCC    1320

AGGAGCTTGG AGCATTGCAG GCTGCAGGCA GAGAGGGCCT GGGCAGGATA CTCAACCTGA    1380

GGGGCTTAAA GGGAGTGGGT TCGGGACCTT TTGGAGACTA TTGGAACAGA GGCACCCCAG    1440

ATCAGGTCCT TCTCTTAGGT GGGACTGCTG TGGTTACCGG CAACTCTTCA TCTGCCCGAG    1500

GTTTGGCCAC ATTAAAACTG TTTGGGATAG GGTGAGGAC AAAGCAGCCT GGCTGGGGGA     1560

GAGTGGGAAT AGGAATGGGG ACATAGTGGC CTGGACTGGG GAAAGTGGGG TGGGATGCGC    1620

GGTATTTCTA AGGAAGAGCC TGAGTTCTGG AGCAGAGCCA GTGGCCACAC TTGACCCTAG    1680

GTCCTCCCCC AAGGCACAGA CGTCACTGGG ATGATTCTTA AGCTCCTAAT CGTCCCGAAT    1740

CAGTGTGAAG GGATTTGGGG ATGGGTGGTT TGAGGTGGCT GCATGCTCCT TTGCCCTTGA    1800

AAACGAATAC TCCATGCTGC AGACTCACAG AGAAGCTCAT GAGGTCTTTG TACTTTTAGG    1860

ACACACTTGT CCTCAGGACA ATTGTCATAT GTCCAGCAAG TGAAGAGACC TATTCAAAGC    1920

TCCACAGCAG TGACAGTTCA TGCAGGCAGG ATAACGTGCG TGTTGGAAGT GGATAGGATT    1980

TGTGTTTAGG GGGTGAAGGG TCAGGCCTAA GAATGCAGGG GCTCCTCTCC CTCAGATGGT    2040

ATTATCCTCT CGGATCTTAC CCGAGCTTTT CACCTAAACA AAAGACCTAA GTCAAGAGGC    2100

AGGTCTGTTT GCCCCCTCTG TCCTCAGTTT ACACTTGTCT CCAACACATG TCTCAGGCTC    2160

ACTTTGGGCT GGTACGCCCC CTCCCCTCTA ACACACAGCC CTCCACTCCC CTCAACAAGA    2220

GCGGGGGGT CAGAAAGCCC GCCGCTGAAA GGTCAGGTCT TGTGTTTCAT TTCTGCAACC    2280

TCTTCGTGGC CAGGTCCAGG GTGGCGTGTG GCTGCTGAGC CCCCGCCTCT GTGACACCCT    2340

CATGGCCATG GACGTCATGC TGTGCACCGC CTCCATCTTC AACCTGTGCG CCATCAGCGT    2400

GGACAGGTGG GTACCCCGGA CGACCCGTCT CTTCCATTCC CATCTTCCGG TCAGCTGCTC    2460

CATTCGGCGG CCTCACCACT CCTGTGCTCC TTCCTCTAGG TTTGTGGCTG TGACCGTGCC    2520

ACTGCGCTAC AACCAGCAGG GTCAGTGCCA GCTGCTGCTC ATCGCCGCCA CGTGGCTGCT    2580

GTCTGCCGCG GTGGCTGCGC CGTCGTGTG CGGCCTCAAT GATGTGCCCG GTCGCGATCC    2640

AACCGTGTGC TGCCTGGAGG ACCGCGACTA CGTGGTCTAC TCATCCATTT GTTCCTTCTT    2700

CCTGCCCTGT CCGCTCATGC TACTGCTTTA CTGGGCCACT TTCCGTGGCT TGCGGCGCTG    2760

GGAGGCAGCC CGGCACACCA AGCTTCACAG CCGCGCGCCG CGCCGACCCA GCGGCCCGGG    2820

CCCGCCGGTG TCGGACCCTA CTCAGGGTCC CCTCTTCTCA GATTGTCCGC CTCCCTCACC    2880

CAGCCTCCGG ACGAGCCCCA CCGTCTCCAG CAGACCAGAG TCAGACCTCT CTCAGAGCCC    2940

CTGCAGCCCC GGGTGTCTGC TCCCTGATGC AGCGCTCGCG CAACCGCCTG CGCCGTCTTC    3000

CCGCAGAAAG AGAGGCGCCA AGATCACTGG AAGGGAGCGC AAGGCGATGA GAGTCCTGCC    3060

GGTGGTAGTT GGTGGGTTTC CGCCCTGGGA CAAGAGCTGA TAGAGGGAGG GGTCCCGGGA    3120

GCCGAGGAGG GAAGGGGGAA GGGTCCAGTT TGGAAGGGTG AAAGGTGGGG GACGGGGGTT    3180

CCTGGTTGAG AGACCTCGAG TGCAGGTGTC CTGGGTGAGG GACCTTGAGT GCAGGTGTAT    3240

AGCTCACGCC GCCCACCCCC AGGCCCCTTC CTGATGTGTT GGACGCCTTT CTTCGTGGTG    3300

CACATCACAC GGGCGCTGTG TCCGGCTTGT TTCGTGTCCC CACGCCTGGT CAGTGCTGTC    3360

ACCTGGCTGG GCTATGTCAA CAGTGCCCTC AACCCCATCA TCTACACCAT CTTCAATGCC    3420

GAGTTTCGAA GTGTCTTCCG CAAGACTCTT CGTCTCCGCT GCTGAAAGAA CCGCTGATGT    3480
```

```
CTTGAGGTCA AGGGGTTCCA AGCCTGTGTG CAGAGTGCGC TGGCGGCTTT CGTTCGTCTG    3540

ATTAAATGAA GTCTTTCCTA ACCATTTATC AACGCTGGGG GCTGGGAAAA AGTAAGGAAA    3600

AGAGGGAGGT CTTTTGTCTG GATGATGGGC CCGGCTAACT TCTGCCTTTG AGGATGCTGC    3660

CGGTTCAGCT CCAGGAGGCA GGAGGCTTCA GAAGTCTTTG CCCTGGAGGA GTAGGGGACC    3720

GACTACATCT GCCTTAGTTT CCGCTCAACA TGAAAAATGA CCAAGTGTTC TCCTGGGAGA    3780

GGAGCTAGAG GAATTTCCTG AGGCTCCTGG GTCCCCAGGA TCCTGTCCAG GCCTTGCTCC    3840

TTGGAGAGCT AGGGAGGGAG GGCTCTTCTG TCATTGATGG GGGAGGGGAT TCCCATTTCA    3900

GAAGCTT                                                              3907
```

(2) INFORMATION FOR SEQ ID NO:2:

(i) SEQUENCE CHARACTERISTICS:
        (A) LENGTH: 385 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (v) FRAGMENT TYPE: N-terminal (vi) ORIGINAL SOURCE:
        (A) ORGANISM: Rattus norvegicus
        (F) TISSUE TYPE: Cardiac muscle (ix) FEATURE:
        (A) NAME/KEY: Protein
        (B) LOCATION: 1..385
        (D) OTHER INFORMATION: /note= "Protein encoded by cDNA for
            D4 receptor"

(x) PUBLICATION INFORMATION:
        (A) AUTHORS: O'Malley, K. L.
            Harmon, S.
            Tang, L.
            Todd, R. D.
        (B) TITLE: The rat dopamine D4 receptor: sequence, gene
            structure and demonstration of expression in the
            cardiovascular system.
        (C) JOURNAL: New Biol.
        (D) VOLUME: 4
        (F) PAGES: 1-9
        (G) DATE: 1992
        (K) RELEVANT RESIDUES IN SEQ ID NO:2: FROM 1 TO 385

(xi) SEQUENCE DESCRIPTION: SEQ ID NO:2:

```
Met Gly Asn Ser Ser Ala Thr Gly Asp Gly Gly Leu Leu Ala Gly Arg
1               5                   10                  15

Gly Pro Glu Ser Leu Gly Thr Gly Thr Gly Leu Gly Gly Ala Gly Ala
            20                  25                  30

Ala Ala Leu Val Gly Gly Val Leu Leu Ile Gly Met Val Leu Ala Gly
        35                  40                  45

Asn Ser Leu Val Cys Val Ser Val Ala Ser Glu Arg Ile Leu Gln Thr
    50                  55                  60

Pro Thr Asn Tyr Phe Ile Val Ser Leu Ala Ala Ala Asp Leu Leu Leu
65                  70                  75                  80

Ala Val Leu Val Leu Pro Leu Phe Val Tyr Ser Glu Gly Gly Val Trp
                85                  90                  95

Leu Leu Ser Pro Arg Leu Cys Asp Thr Leu Met Ala Met Asp Val Met
```

```
                100             105             110
Leu Cys Thr Ala Ser Ile Phe Asn Leu Cys Ala Ile Ser Val Asp Arg
            115             120             125
Phe Val Ala Val Thr Val Pro Leu Arg Tyr Asn Gln Gln Gly Gln Cys
    130             135             140
Gln Leu Leu Leu Ile Ala Ala Thr Trp Leu Leu Ser Ala Ala Val Ala
145             150             155             160
Ala Pro Val Val Cys Gly Leu Asn Asp Val Pro Gly Arg Asp Pro Thr
                165             170             175
Val Cys Cys Leu Glu Asp Arg Asp Tyr Val Val Tyr Ser Ser Ile Cys
            180             185             190
Ser Phe Phe Leu Pro Cys Pro Leu Met Leu Leu Leu Tyr Trp Ala Thr
    195             200             205
Phe Arg Gly Leu Arg Arg Trp Glu Ala Ala Arg His Thr Lys Leu His
210             215             220
Ser Arg Ala Pro Arg Arg Pro Ser Gly Pro Gly Pro Pro Val Ser Asp
225             230             235             240
Pro Thr Gln Gly Pro Leu Phe Ser Asp Cys Pro Pro Pro Ser Pro Ser
                245             250             255
Leu Arg Thr Ser Pro Thr Val Ser Ser Arg Pro Glu Ser Asp Leu Ser
            260             265             270
Gln Ser Pro Cys Ser Pro Gly Cys Leu Leu Pro Asp Ala Ala Leu Ala
    275             280             285
Gln Pro Pro Ala Pro Ser Ser Arg Arg Lys Arg Gly Ala Lys Ile Thr
    290             295             300
Gly Arg Glu Arg Lys Ala Met Arg Val Leu Pro Val Val Val Gly Pro
305             310             315             320
Phe Leu Met Cys Trp Thr Pro Phe Phe Val Val His Ile Thr Arg Ala
                325             330             335
Leu Cys Pro Ala Cys Phe Val Ser Pro Arg Leu Val Ser Ala Val Thr
            340             345             350
Trp Leu Gly Tyr Val Asn Ser Ala Leu Asn Pro Ile Ile Tyr Thr Ile
    355             360             365
Phe Asn Ala Glu Phe Arg Ser Val Phe Arg Lys Thr Leu Arg Leu Arg
    370             375             380
Cys
385

(2) INFORMATION FOR SEQ ID NO:3:

(i) SEQUENCE CHARACTERISTICS:
        (A) LENGTH: 1367 base pairs
        (B) TYPE: nucleic acid
        (C) STRANDEDNESS: single
        (D) TOPOLOGY: linear (ii) MOLECULE TYPE: mRNA (iii) HYPOTHETICAL: NO (iv) ANTI-SENSE: NO (vi) ORIGINAL SOURCE:
        (A) ORGANISM: Homo sapiens (ix) FEATURE:
        (A) NAME/KEY: misc_feature
        (B) LOCATION: 1..1367
        (D) OTHER INFORMATION: /note= "D4 Dopamine Receptor cDNA"
```

(x) PUBLICATION INFORMATION:
    (A) AUTHORS: Van tol, H. H.
        Bunzow, J. R.
        Guan, H. C.
        Sunahara, R. K.
        Seeman, P.
        Niznik, H. B.
        Civelli, O.
    (B) TITLE: Cloning of the gene for a human dopamine D4 receptor with high affinity for the antipsychotic clozapine.
    (C) JOURNAL: Nature
    (D) VOLUME: 350
    (F) PAGES: 610-614
    (G) DATE: 1991
    (K) RELEVANT RESIDUES IN SEQ ID NO:3: FROM 1 TO 1367

(xi) SEQUENCE DESCRIPTION: SEQ ID NO:3:

```
CGGGGGCGGG ACCAGGGTCC GGCCGGGGCG TGCCCCCGGG GAGGGACTCC CCGGCTTGCC      60
CCCCGGCGTT GTCCGCGGTG CTCAGCGCCC GCCCGGGCGC GCCATGGGGA ACCGCAGCAC     120
CGCGGACGCG GACGGGCTGC TGGCTGGGCG CGGGCCGGCC GCGGGGGCAT CTGCGGGGGC     180
ATCTGCGGGG CTGGCTGGGC AGGGCGCGGC GGCGCTGGTG GGGGGCGTGC TGCTCATCGG     240
CGCGGTGCTC GCGGGGAACT CGCTCGTGTG CGTGAGCGTG GCCACCGAGC GCGCCCTGCA     300
GACGCCCACC AACTCCTTCA TCGTGAGCCT GGCGGCCGCC GACCTCCTCC TCGCTCTCCT     360
GGTGCTGCCG CTCTTCGTCT ACTCCGAGGT CCAGGGTGGC GCGTGGCTGC TGAGCCCCCG     420
CCTGTGCGAC GCCCTCATGG CCATGGACGT CATGCTGTGC ACCGCCTCCA TCTTCAACCT     480
GTGCGCCATC AGCGTGGACA GGTTCGTGGC CGTGGCCGTG CCGCTGCGCT ACAACCGGCA     540
GGGTGGGAGC CGCCGGCAGC TGCTGCTCAT CGGCGCCACG TGGCTGCTGT CCGCGGCGGT     600
GGCGGCGCCC GTACTGTGCG GCCTCAACGA CGTGCGCGGC CGCGACCCCG CCGTGTGCCG     660
CCTGGAGGAC CGCGACTACG TGGTCTACTC GTCCGTGTGC TCCTTCTTCC TACCCTGCCC     720
GCTCATGCTG CTGCTCTACT GGGCCACGTT CCGCGGCCTG CAGCGCTGGG AGGTGGCACG     780
TCGCGCCAAG CTGCACGGCC GCGCGCCCCG CCGACCCAGC GGCCCTGGCC CGCCTTCCCC     840
CACGCCACCC GCGCCCCGCC TCCCCCAGGA CCCCTGCGGC CCCGACTGTG CGCCCCCCGC     900
GCCCGGCCTC CCCCCGGACC CCTGCGGCTC CAACTGTGCT CCCCCCGACG CCGTCAGAGC     960
CGCCGCGCTC CCACCCCAGA CTCCACCGCA GACCCGCAGG AGGCGGCGTG CCAAGATCAC    1020
CGGCCGGGAG CGCAAGGCCA TGAGGGTCCT GCCGGTGGTG GTCGGGGCCT TCCTGCTGTG    1080
CTGGACGCCC TTCTTCGTGG TGCACATCAC GCAGGCGCTG TGTCCTGCCT GCTCCGTGCC    1140
CCCGCGGCTG GTCAGCGCCG TCACCTGGCT GGGCTACGTC AACAGCGCCC TCAACCCCGT    1200
CATCTACACT GTCTTCAACG CCGAGTTCCG CAACGTCTTC CGCAAGGCCC TGCGTGCCTG    1260
CTGCTGAGCC GGGCACCCCC GGACGCCCCC CGGCCTGATG CCAGGCCTC AGGGACCAAG    1320
GAGATGGGGA GGGCGCTTTT GTACGTTAAT TAAACAAATT CCTTCCC                 1367
```

(2) INFORMATION FOR SEQ ID NO:4:

(i) SEQUENCE CHARACTERISTICS:
        (A) LENGTH: 387 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (v) FRAGMENT TYPE: N-terminal (vi) ORIGINAL SOURCE:
            (A) ORGANISM: Homo sapiens (ix) FEATURE:
            (A) NAME/KEY: Protein
            (B) LOCATION: 1..387
            (D) OTHER INFORMATION: /note= "Human D4 Receptor Protein"

(xi) SEQUENCE DESCRIPTION: SEQ ID NO:4:

```
Met Gly Asn Arg Ser Thr Ala Asp Ala Asp Gly Leu Leu Ala Gly Arg
1               5                   10                  15

Gly Pro Ala Ala Gly Ala Ser Ala Gly Ala Ser Ala Gly Leu Ala Gly
            20                  25                  30

Gln Gly Ala Ala Ala Leu Val Gly Gly Val Leu Leu Ile Gly Ala Val
        35                  40                  45

Leu Ala Gly Asn Ser Leu Val Cys Val Ser Val Ala Thr Glu Arg Ala
50                  55                  60

Leu Gln Thr Pro Thr Asn Ser Phe Ile Val Ser Leu Ala Ala Ala Asp
65                  70                  75                  80

Leu Leu Leu Ala Leu Leu Val Leu Pro Leu Phe Val Tyr Ser Glu Val
                85                  90                  95

Gln Gly Gly Ala Trp Leu Leu Ser Pro Arg Leu Cys Asp Ala Leu Met
            100                 105                 110

Ala Met Asp Val Met Leu Cys Thr Ala Ser Ile Phe Asn Leu Cys Ala
        115                 120                 125

Ile Ser Val Asp Arg Phe Val Ala Val Ala Val Pro Leu Arg Tyr Asn
130                 135                 140

Arg Gln Gly Gly Ser Arg Arg Gln Leu Leu Leu Ile Gly Ala Thr Trp
145                 150                 155                 160

Leu Leu Ser Ala Ala Val Ala Ala Pro Val Leu Cys Gly Leu Asn Asp
                165                 170                 175

Val Arg Gly Arg Asp Pro Ala Val Cys Arg Leu Glu Asp Arg Asp Tyr
            180                 185                 190

Val Val Tyr Ser Ser Val Cys Ser Phe Phe Leu Pro Cys Pro Leu Met
        195                 200                 205

Leu Leu Leu Tyr Trp Ala Thr Phe Arg Gly Leu Gln Arg Trp Glu Val
210                 215                 220

Ala Arg Arg Ala Lys Leu His Gly Arg Ala Pro Arg Arg Pro Ser Gly
225                 230                 235                 240

Pro Gly Pro Pro Ser Pro Thr Pro Pro Ala Pro Arg Leu Pro Gln Asp
                245                 250                 255

Pro Cys Gly Pro Asp Cys Ala Pro Pro Ala Pro Gly Leu Pro Pro Asp
            260                 265                 270

Pro Cys Gly Ser Asn Cys Ala Pro Pro Asp Ala Val Arg Ala Ala Ala
        275                 280                 285

Leu Pro Pro Gln Thr Pro Pro Gln Thr Arg Arg Arg Arg Arg Ala Lys
290                 295                 300

Ile Thr Gly Arg Glu Arg Lys Ala Met Arg Val Leu Pro Val Val Val
305                 310                 315                 320

Gly Ala Phe Leu Leu Cys Trp Thr Pro Phe Phe Val Val His Ile Thr
                325                 330                 335

Gln Ala Leu Cys Pro Ala Cys Ser Val Pro Pro Arg Leu Val Ser Ala
            340                 345                 350
```

```
Val Thr Trp Leu Gly Tyr Val Asn Ser Ala Leu Asn Pro Val Ile Tyr
        355                 360                 365

Thr Val Phe Asn Ala Glu Phe Arg Asn Val Phe Arg Lys Ala Leu Arg
    370                 375                 380

Ala Cys Cys
385
```

(2) INFORMATION FOR SEQ ID NO:5:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: misc_feature
        (B) LOCATION: 1..18
        (D) OTHER INFORMATION: /note= "Synthetic oligonucleotide
            primer - Tm VI/VII primer set orD-403"

(x) PUBLICATION INFORMATION:
        (A) AUTHORS: O'Malley, K. L.
            Harmon, S.
            Tang, L.
            Todd, R. D.
        (B) TITLE: The rat dopamine D4 receptor: sequence, gene
            structure and demonstration of expression in the
            cardiovascular system.
        (C) JOURNAL: New Biol.
        (D) VOLUME: 4
        (F) PAGES: 1-9
        (G) DATE: 1992
        (K) RELEVANT RESIDUES IN SEQ ID NO:5: FROM 1 TO 18

(xi) SEQUENCE DESCRIPTION: SEQ ID NO:5:

```
TGCTGGCTGC CCTTCTTC                                                 18
```

(2) INFORMATION FOR SEQ ID NO:6:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: misc_feature
        (B) LOCATION: 1..18
        (D) OTHER INFORMATION: /note= "Synthetic oligonucleotide
            primer - TM VI in both D2 and D3 genes and or
            D-404."

(x) PUBLICATION INFORMATION:
        (A) AUTHORS: O'Malley, K. L.
            Harmon, S.
            Tang, L.
            Todd, R. D.
        (B) TITLE: The rat dopamine D4 receptor: sequence, gene
            structure and demonstration of expression in the
            cardiovascular system.
        (C) JOURNAL: New Biol.

```
            (D) VOLUME: 4
            (F) PAGES: 1-9
            (G) DATE: 1991
            (K) RELEVANT RESIDUES IN SEQ ID NO:6: FROM 1 TO 18

(xi) SEQUENCE DESCRIPTION: SEQ ID NO:6:

GAAGCCTTTG CGGAACTC                                                   18

(2) INFORMATION FOR SEQ ID NO:7:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (ix) FEATURE:
            (A) NAME/KEY: misc_feature
            (B) LOCATION: 1..18
            (D) OTHER INFORMATION: /note= "Synthetic oligonucleotide
                primer - reverse transcribed using orD4-515, and
                is complementary to nucleotides 366 to 383 in (x) PUBLICATION INFORMATION:
            (A) AUTHORS: O'Malley, K. L.
                Harmon, S.
                Tang, L.
                Todd, R. D.
            (B) TITLE: The rat dopamine D4 receptor: sequence, gene
                structure and demonstration of expression in the
                cardiovascular system.
            (C) JOURNAL: New Biol.
            (D) VOLUME: 4
            (F) PAGES: 1-9
            (G) DATE: 1992
            (K) RELEVANT RESIDUES IN SEQ ID NO:7: FROM 1 TO 18

(xi) SEQUENCE DESCRIPTION: SEQ ID NO:7:

CTGTCCACGC TGATGGCG                                                   18

(2) INFORMATION FOR SEQ ID NO:8:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (ix) FEATURE:
            (A) NAME/KEY: misc_feature
            (B) LOCATION: 1..18
            (D) OTHER INFORMATION: /note= "Synthetic oligonucleotide
                primer - utilized orD4-465 and orD4-466 and is
                identical to nucleotides 187 to 204 in Sequence (x) PUBLICATION INFORMATION:
            (A) AUTHORS: O'Malley, K. L.
                Harmon, S.
                Tang, L.
                Todd, R. D.
            (B) TITLE: The rat dopamine D4 receptor: sequence, gene
                structure and demonstration of expression in the
                cardiovascular system.
```

```
            (C) JOURNAL: New Biol.
            (D) VOLUME: 4
            (F) PAGES: 1-9
            (G) DATE: 1992
            (K) RELEVANT RESIDUES IN SEQ ID NO:8: FROM 1 TO 18

(xi) SEQUENCE DESCRIPTION: SEQ ID NO:8:

CAGACACCGA CCAACTAC                                                    18

(2) INFORMATION FOR SEQ ID NO:9:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (ix) FEATURE:
            (A) NAME/KEY: misc_feature
            (B) LOCATION: 1..18
            (D) OTHER INFORMATION: /note= "Synthetic oligonucleotide
                primer - included orD4-474 and is identical to
                nucleotides 309 to 326 in Sequence I.D. No. 1."

(x) PUBLICATION INFORMATION:
            (A) AUTHORS: O'Malley, K. L.
                Harmon, S.
                Tang, L.
                Todd, R. D.
            (B) TITLE: The rat dopamine D4 receptor: sequence, gene
                structure and demonstration of expression in the
                cardiovascular system.
            (C) JOURNAL: New Biol.
            (D) VOLUME: 4
            (F) PAGES: 1-9
            (G) DATE: 1992
            (K) RELEVANT RESIDUES IN SEQ ID NO:9: FROM 1 TO 18

(xi) SEQUENCE DESCRIPTION: SEQ ID NO:9:

TGACACCCTC ATGGCCAT                                                    18

(2) INFORMATION FOR SEQ ID NO:10:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (ix) FEATURE:
            (A) NAME/KEY: misc_feature
            (B) LOCATION: 1..18
            (D) OTHER INFORMATION: /note= "Synthetic oligonucleotide
                primer - included orD4-465 and is complementary to
                nucleotides 342 to 359 in Sequence I.D. No. 1."

(x) PUBLICATION INFORMATION:
            (A) AUTHORS: O'Malley, K. L.
                Harmon, S.
                Tang, L.
                Todd, R. D.
            (B) TITLE: The rat dopamine D4 receptor: sequence, gene
                structure and demonstration of expression in the
```

```
                    cardiovascular system.
        (C) JOURNAL: New Biol.
        (D) VOLUME: 4
        (F) PAGES: 1-9
        (G) DATE: 1992
        (K) RELEVANT RESIDUES IN SEQ ID NO:10: FROM 1 TO 18

(xi) SEQUENCE DESCRIPTION: SEQ ID NO:10:

TTGAAGATGG AGGGGGTG                                                   18

(2) INFORMATION FOR SEQ ID NO:11:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: misc_feature
        (B) LOCATION: 1..18
        (D) OTHER INFORMATION: /note= "Synthetic oligonucleotide
            primer - included orD4-501 and is identical to
            nucleotides 657 to 674 in Sequence I.D. No. 1."

(x) PUBLICATION INFORMATION:
        (A) AUTHORS: O'Malley, K. L.
            Harmon, S.
            Tang, L.
            Todd, R. D.
        (B) TITLE: The rat dopamine D4 receptor: sequence, gene
            structure and demonstration of expression in the
            cardiovascular system.
        (C) JOURNAL: New Biol.
        (D) VOLUME: 4
        (F) PAGES: 1-9
        (G) DATE: 1992
        (K) RELEVANT RESIDUES IN SEQ ID NO:11: FROM 1 TO 18

(xi) SEQUENCE DESCRIPTION: SEQ ID NO:11:

GCACACCAAG CTTCACAG                                                   18

(2) INFORMATION FOR SEQ ID NO:12:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: misc_feature
        (B) LOCATION: 1..23
        (D) OTHER INFORMATION: /note= "Synthetic oligonucleotide
            primer - included orD4-506 and is complementary to
            nucleotides 1064 to 1085 in Sequence I.D. No. 1."

(x) PUBLICATION INFORMATION:
        (A) AUTHORS: O'Malley, K. L.
            Harmon, S.
            Tang, L.
            Todd, R. D.
        (B) TITLE: The rat dopamine D4 receptor: sequence, gene
``` structure and demonstration of expression in the
          cardiovascular system.
       (C) JOURNAL: New Biol.
       (D) VOLUME: 4
       (F) PAGES: 1-9
       (G) DATE: 1992
       (K) RELEVANT RESIDUES IN SEQ ID NO:12: FROM 1 TO 23

(xi) SEQUENCE DESCRIPTION: SEQ ID NO:12:

TTGAAGGGCA CTGTTGACAT AGC                                               23

(2) INFORMATION FOR SEQ ID NO:13:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: misc_feature
        (B) LOCATION: 1..24
        (D) OTHER INFORMATION: /note= "Synthetic oligonucleotide
            included orD-502 and is identical to nucleotides
            124 to 193 in Sequence I.D. No. 1."

(x) PUBLICATION INFORMATION:
        (A) AUTHORS: O'Malley, K. L.
            Harmon, S.
            Tang, L.
            Todd, R. D.
        (B) TITLE: The rat dopamine D4 receptor: sequence, gene
            structure and demonstration of expression in the
            cardiovascular system.
        (C) JOURNAL: New Biol.
        (D) VOLUME: 4
        (F) PAGES: 1-9
        (G) DATE: 1992
        (K) RELEVANT RESIDUES IN SEQ ID NO:13: FROM 1 TO 24

(xi) SEQUENCE DESCRIPTION: SEQ ID NO:13:

ATGGTGTTGG CAGGGAACTC GCTC                                              24

(2) INFORMATION FOR SEQ ID NO:14:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: misc_feature
        (B) LOCATION: 1..24
        (D) OTHER INFORMATION: /note= "Synthetic oligonucleotide
            included orD-499 and is complementary to
            nucleotides 124 to 193 in Sequence I.D. No. 1."

(x) PUBLICATION INFORMATION:
        (A) AUTHORS: O'Malley, K. L.
            Harmon, S.
            Tang, L.
            Todd, R. D.

(B) TITLE: The rat dopamine D4 receptor: sequence, gene
    structure and demonstration of expression in the
    cardiovascular system.
(C) JOURNAL: New Biol.
(D) VOLUME: 4
(F) PAGES: 1-9
(G) DATE: 1992
(K) RELEVANT RESIDUES IN SEQ ID NO:14: FROM 1 TO 24

(xi) SEQUENCE DESCRIPTION: SEQ ID NO:14:

GAGCGAGTTC CCTGCCAACA CCAT                                                24

(2) INFORMATION FOR SEQ ID NO:15:

(i) SEQUENCE CHARACTERISTICS:
        (A) LENGTH: 2428 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
         (A) ORGANISM: Rattus norvegicus
         (F) TISSUE TYPE: Cardiac Muscle (ix) FEATURE:
         (A) NAME/KEY: misc_feature
         (B) LOCATION: 1..2428
         (D) OTHER INFORMATION: /note= "Rat d2 receptor sequence"

(x) PUBLICATION INFORMATION:
        (A) AUTHORS: Bunzow, J. R.
                     Van Tol, H. H.M.
                     Grandy, D. K.
                     Albert, P.
                     Salon, J.
                     Christie, M.
                     Machida, C. A.
                     Neve, K. A.
                     Civelli, O.
        (B) TITLE: Cloning and expression of a rat D2 dopamine
            receptor cDNA.
        (C) JOURNAL: Nature
        (D) VOLUME: 336
        (F) PAGES: 783-787
        (G) DATE: 1988
        (K) RELEVANT RESIDUES IN SEQ ID NO:15: FROM 1 TO 2428

(xi) SEQUENCE DESCRIPTION: SEQ ID NO:15:

CCACCCAGTG GCCCCACTGC CCAATGGAT CCACTGAACC TGTCCTGGTA CGATGACGAT       60

CTGGAGAGGC AGAACTGGAG CCGGCCCTTC AATGGGTCAG AAGGGAAGGC AGACAGGCCC      120

CACTACAACT ACTATGCCAT GCTGCTCACC CTCCTCATCT TTATCATCGT CTTTGGCAAT      180

GTGCTGGTGT GCATGGCTGT ATCCCGAGAG AAGGCTTTGC AGACCACCAC CAACTACTTG      240

ATAGTCAGCC TTGCTGTGGC TGATCTTCTG GTGGCCACAC TGGTAATGCC GTGGGTTGTC      300

TACCTGGAGG TGGTGGGTGA GTGGAAATTC AGCAGGATTC ACTGTGACAT CTTTGTCACT      360

CTGGATGTCA TGATGTGCAC AGCAAGCATC CTGAACCTGT GTGCCATCAG CATTGACAGG      420

TACACAGCTG TGGCAATGCC CATGCTGTAT AACACACGCT ACAGCTCCAA GCGCCGAGTT      480

ACTGTCATGA TTGCCATTGT CTGGGTCCTG TCCTTCACCA TCTCCTGCCC ACTGCTCTTC      540

GGACTCAACA ATACAGACCA GAATGAGTGT ATCATTGCCA ACCCTGCCTT TGTGGTCTAC      600

TCCTCCATTG TCTCATTCTA CGTGCCCTTC ATCGTCACTC TGCTGCTGTA TATCAAAATC      660

-continued

```
TACATCGTCC TCCGGAAGCG CCGGAAGCGG GTCAACACCA AGCGCAGCAG TCGAGCTTTC      720

AGAGCCAACC TGAAGACACC ACTCAAGGGC AACTGTACCC ACCCTGAGGA CATGAAACTC      780

TGCACCGTTA TCATGAAGTC TAATGGGAGT TTCCCAGTGA ACAGGCGGAG AATGGATGCT      840

GCCCGCCGAG CTCAGGAGCT GGAAATGGAG ATGCTGTCAA GCACCAGCCC CCCAGAGAGG      900

ACCCGGTATA GCCCCATCCC TCCCAGTCAC CACCAGCTCA CTCTCCCTGA TCCATCCCAC      960

CACGGCCTAC ATAGCAACCC TGACAGTCCT GCCAAACCAG AGAAGAATGG GCACGCCAAG     1020

ATTGTCAATC CCAGGATTGC CAAGTTCTTT GAGATCCAGA CCATGCCCAA TGGCAAAACC     1080

CGGACCTCCC TTAAGACGAT GAGCCGCAGA AAGCTCTCCC AGCAGAAGGA GAAGAAAGCC     1140

ACTCAGATGC TTGCCATTGT TCTCGGTGTG TTCATCATCT GCTGGCTGCC CTTCTTCATC     1200

ACGCACATCC TGAATATACA CTGTGATTGC AACATCCCAC CAGTCCTCTA CAGCGCCTTC     1260

ACATGGCTGG GCTATGTCAA CAGTGCCGTC AACCCCATCA TCTACACCAC CTTCAACATC     1320

GAGTTCCGCA AGGCCTTCAT GAAGATCTTG CACTGCTGAG TCTGCCCCTT GCCTGCACAG     1380

CAGCTGCTTC CCACCTCCCT GCCTATGCAG GCCAGACCTC ATCCCTGCAA GCTGTGGGCA     1440

GAAAGGCCCA GATGGACTTG GCCTTCTCTC GACCCTGCAG GCCCTGCAGT GTTAGCTTGG     1500

CTCGATGCCC CTCTCTGCCC ACACACCCTC ATCCTGCCAG GGTAGGGCCA GGGAGACTGG     1560

TATCTTACCA GCTCTGGGGT TGGACCCATG GCTCAGGGCA GCTCACAGAG TGCCCCTCTC     1620

ATATCCAGAC CCTGTCTCCT TGGCACCAAA GATGCAGCGG CCTTCCTTGA CCTTCCTCTT     1680

GGGCACAGAA ACTAGCTCAG TGGTCGAGCA CACCCTGATC GCTGGCTTGG CCTGGCCCTT     1740

GCTTGCCTGT GCCAGATCAG GTGGTGGGAG GGAGCAACAG TTCTTACTTT ATAGGAACCA     1800

CATAGGAAAG CAGGGAACAC GCCAAGTCCT CCAGGCAACA TCAGTGTCAG GAGACACACA     1860

TAAACACCAG GTAGCTCCAT GGACCCCAGA GAAACTGAGG CTGAAAAATC TGTTTTCCAC     1920

TCCAACTCTA GTGTGAGTCC CTACTTTTCA TAGCCATGGG TATTACTATG TCCTACCTTG     1980

TTATAGTATC CCATGGGGTT TCTGTACCAT TTGGGGAAA ACAACTCTAA TCCTCAAGGG      2040

CCCCAAGAGA ATCTGTAAGG AGAAAAATAG GCTGATCTCC CTCTACTCTC CAATCCACTC     2100

CACCACTTCT TGATATACCT TGGATGTATC CATTCCTCAC AGCAAATGCT GGCCAGTCAG     2160

GCCTTGGACC AGTGTTGGAG TTGAAGCTGG ATGTGGTAAC TTGGGGCTCT TTGGGGCTGG     2220

GGGGGTTGTT AACATCGTCT CTCTTCCATA TCTCTTCCTT CCCAGTGCCT CTGCCTTAGA     2280

AGAGGCTGTG GATGGGGTGC TGGGACTGCT GATACCATTG GGCCTGGCTG AATGAGGAGG     2340

GGAAGCTGCA GTTTGGAGGG TTCTGGGATC CAACTCTGTA ACATCACTAT ACCTGCACCA     2400

AAACTAATAA AACCTTGACA AGAGTCAA                                        2428
```

(2) INFORMATION FOR SEQ ID NO:16:

(i) SEQUENCE CHARACTERISTICS:
        (A) LENGTH: 1261 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Homo sapiens (ix) FEATURE:

(A) NAME/KEY: misc_feature
        (B) LOCATION: 1..1261
        (D) OTHER INFORMATION: /note= "Human d3 cDNA"

(x) PUBLICATION INFORMATION:
        (A) AUTHORS: Giros, B.
            Martres, M. P.
            Sokoloff, P.
            Schwartz, J. C.
        (C) JOURNAL: C.R. Acad. Sci. (Paris) III
        (D) VOLUME: 311
        (F) PAGES: 501-508
        (G) DATE: 1990
        (K) RELEVANT RESIDUES IN SEQ ID NO:16: FROM 1 TO 1261

(xi) SEQUENCE DESCRIPTION: SEQ ID NO:16:

| | | | | | |
|---|---|---|---|---|---|
| TGGGCTATGG | CATCTCTGAG | TCAGCTGAGT | AGCCACCTGA | ACTACACCTG | TGGGGCAGAG | 60 |
| AACTCCACAG | GTGCCAGCCA | GGCCCGCCCA | CATGCCTACT | ATGCCCTCTC | CTACTGCGCG | 120 |
| CTCATCCTGG | CCATCGTCTT | CGGCAATGGC | CTGGTGTGCA | TGGCTGTGCT | GAAGGAGCGG | 180 |
| GCCCTGCAGA | CTACCACCAA | CTACTTAGTA | GTGAGCCTGG | CTGTGGCAGA | CTTGCTGGTG | 240 |
| GCCACCTTGG | TGATGCCCTG | GGTGGTATAC | CTGGAGGTGA | CAGGTGGAGT | CTGGAATTTC | 300 |
| AGCCGCATTT | GCTGTGATGT | TTTTGTCACC | CTGGATGTCA | TGATGTGTAC | AGCCAGCATC | 360 |
| CTTAATCTCT | GTGCCATCAG | CATAGACAGG | TACACTGCAG | TGGTCATGCC | CGTTCACTAC | 420 |
| CAGCATGGCA | CGGGACAGAG | CTCCTGTCGG | CGCGTGGCCC | TCATGATCAC | GGCCGTCTGG | 480 |
| GTACTGGCCT | TTGCTGTGTC | CTGCCCTCTT | CTGTTTGGCT | TTAATACCAC | AGGGGACCCC | 540 |
| ACTGTCTGCT | CCATCTCCAA | CCCTGATTTT | GTCATCTACT | CTTCAGTGGT | GTCCTTCTAC | 600 |
| CTGCCCTTTG | GAGTGACTGT | CCTTGTCTAT | GCCAGAATCT | ATGTGGTGCT | GAAACAAAGG | 660 |
| AGACGGAAAA | GGATCCTCAC | TCGACAGAAC | AGTCAGTGCA | ACAGTGTCAG | GCCTGGCTTC | 720 |
| CCCCAACAAA | CCCTCTCTCC | TGACCCGGCA | CATCTGGAGC | TGAAGCGTTA | CTACAGCATC | 780 |
| TGCCAGGACA | CTGCCTTGGG | TGGACCAGGC | TTCCAAGAAA | GAGGAGGAGA | GTTGAAAAGA | 840 |
| GAGGAGAAGA | CTCGGAATTC | CCTGAGTCCC | ACCATAGCGC | CTAAGCTCAG | CTTAGAAGTT | 900 |
| CGAAAGCTCA | GCAATGGCAG | ATTATCGACA | TCTTTGAAGC | TGGGGCCCCT | GCAACCTCGG | 960 |
| GGAGTGCCAC | TTCGGGAGAA | GAAGGCAACC | CAAATGGTGG | CCATTGTGCT | TGGGGCCTTC | 1020 |
| ATTGTCTGCT | GGCTGCCCTT | CTTCTTGACC | CATGTTCTCA | ATACCCACTG | CCAGACATGC | 1080 |
| CACGTGTCCC | CAGAGCTTTA | CAGTGCCACG | ACATGGCTGG | GCTACGTGAA | TAGCGCCCTC | 1140 |
| AACCCTGTGA | TCTATACCAC | CTTCAATATC | GAGTTCCGGA | AAGCCTTCCT | CAAGATCCTG | 1200 |
| TCTTGCTGAG | GGAGCAGAAG | AGGGAACACT | CTTTGTACCC | ATTTCTAGCT | GCCAGGCTGT | 1260 |
| T | | | | | | 1261 |

We claim:

1. An isolated nucleic acid molecule comprising SEQ ID NO:1.

2. An isolated nucleic acid molecule encoding SEQ ID NO:2.

3. A probe for dopamine receptors comprising at least fourteen contiguous nucleotides of a nucleic acid molecule encoding a rat $D_4$ dopamine receptor as shown in Sequence ID No. 1 between nucleotides 1 and 3263.

4. The probe of claim 3 further comprising a label selected from the group consisting of dyes, radiolabels, tomography positron emission labels, magnetic resonance imaging labels, fluorescent labels, and enzymes.

* * * * *